US007931897B2

(12) United States Patent
Kosaka et al.

(10) Patent No.: US 7,931,897 B2
(45) Date of Patent: Apr. 26, 2011

(54) THERAPEUTIC AGENT FOR HEMATOPOIETIC TUMORS

(75) Inventors: Masaaki Kosaka, Tokushima (JP); Shuji Ozaki, Tokushima (JP); Yuji Wakahara, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 471 days.

(21) Appl. No.: 10/467,358

(22) PCT Filed: Feb. 6, 2002

(86) PCT No.: PCT/JP02/00989
§ 371 (c)(1),
(2), (4) Date: Aug. 7, 2003

(87) PCT Pub. No.: WO02/064159
PCT Pub. Date: Aug. 22, 2002

(65) Prior Publication Data
US 2006/0078539 A1    Apr. 13, 2006

(30) Foreign Application Priority Data

Feb. 7, 2001  (JP) ................. 2001-031492

(51) Int. Cl.
*A61K 38/21*   (2006.01)
*A61K 38/00*   (2006.01)
*A61K 39/395*  (2006.01)
(52) U.S. Cl. ............... 424/133.1; 424/85.6; 424/155.1
(58) Field of Classification Search .............. 424/85.6, 424/133.1, 155.1
See application file for complete search history.

(56) References Cited

U.S. PATENT DOCUMENTS

| 4,401,756 | A | 8/1983 | Gillis |
| 5,328,989 | A | 7/1994 | Vellekamp et al. |
| 5,756,318 | A | 5/1998 | Kosuna |
| 5,830,463 | A | 11/1998 | Duke et al. |
| 6,180,370 | B1 | 1/2001 | Queen et al. |
| 6,258,352 | B1 | 7/2001 | Shimonaka |
| 6,503,510 | B2* | 1/2003 | Koishihara et al. ........ 424/156.1 |
| 2002/0037288 | A1 | 3/2002 | Koishihara et al. |
| 2003/0175281 | A1* | 9/2003 | Kosaka et al. ............ 424/155.1 |
| 2006/0193828 | A1* | 8/2006 | Kosaka et al. ............ 424/85.6 |

FOREIGN PATENT DOCUMENTS

| EP | 0 125 023 | 11/1984 |
| EP | 0 239-400 | 9/1987 |
| EP | 0 256 714 | 2/1988 |
| EP | 0 733 643 | 9/1996 |
| EP | 0 770 628 | 5/1997 |
| EP | 0 960 936 | 12/1999 |
| EP | 0 997 152 | 5/2000 |
| EP | 0 997 152 A1 | 5/2000 |
| JP | 1-59878 | 4/1989 |
| JP | 7-196694 | 1/1995 |
| JP | 7-236475 | 9/1995 |
| WO | WO-83/04313 | 12/1983 |
| WO | WO-92/01047 | 1/1992 |
| WO | WO-92/03918 | 3/1992 |
| WO | WO-92/20791 | 11/1992 |
| WO | WO-93/06213 | 4/1993 |
| WO | WO-93/11236 | 6/1993 |
| WO | WO-93/12227 | 6/1993 |
| WO | WO-93/19172 | 9/1993 |
| WO | WO-94/02602 | 2/1994 |
| WO | 94/06818 A1 | 3/1994 |
| WO | WO 94/06818 * | 3/1994 |
| WO | WO-94/11523 | 5/1994 |
| WO | WO-94/25585 | 11/1994 |
| WO | WO-95/01438 | 1/1995 |
| WO | WO-95/15388 | 6/1995 |
| WO | WO-96/02576 | 2/1996 |
| WO | WO-96/04925 | 2/1996 |
| WO | WO-96/30394 | 3/1996 |
| WO | WO-96/33735 | 10/1996 |
| WO | WO-96/34096 | 10/1996 |
| WO | WO-98/14580 | 4/1998 |
| WO | WO-98/35698 | 8/1998 |
| WO | 99/18997 A1 | 4/1999 |
| WO | WO-99/18997 | 4/1999 |
| WO | 01/13940 A1 | 3/2001 |
| WO | 01/97844 A1 | 12/2001 |

OTHER PUBLICATIONS

Ozaki et al. (Blood 94(10) Suppl. 1:549a (1999).*
Search output from ATCC website for anti-HM1.24 monoclonal antibody/hybridoma deposit (pp. 1-2).*
Fundamental Immunology 242 (William E. Paul, M.D. ed., 3d ed. 1993).*
Sequence search alignment for SEQ ID No. 2 (pp. 1-2).*
Ohtomo et al. (Biochem. Biophys. Res. Comm. 258:583-591 (1999).*
Blasius et al. (J. Immunol. 177:3260-3265 (2006)).*
ATCC data sheet for ARH-77 cell line.*
Stedman's On-line Medical Dictionary, 27th Ed., "myeloma" pp. 1-3 (Mar. 9, 2009).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
S. Ozaki et al., "Humanized Anti-HM1.24 Antibody Mediates Myeloma Cell Cytotoxicity that is Enhanced by Cytokine Stimulation of Effector Cells," *Blood*, vol. 93, No. 11, pp. 3922-3930, 1999.
S. Koenig et al., "Cloning of an Interferon Regulatory Factor 2 Isoform with Different Regulatory Ability," *Nucleic Acids Research*, vol. 28, No. 21, pp. 4219-4224, 2000.

(Continued)

Primary Examiner — Lynn Bristol
(74) Attorney, Agent, or Firm — Morrison & Foerster LLP

(57) ABSTRACT

An inducing agent or enhancing agent, for the expression of HM1.24 antigen in hematopoietic tumor cells, comprising interferon α, interferon γ, or the IRF-2 protein as an active ingredient, as well as an anti-tumor agent for hematopoietic tumors which comprises a combination of said inducing agent or enhancing agent and an antibody against HM1.24.

8 Claims, 13 Drawing Sheets

OTHER PUBLICATIONS

T. Jesse et al., "Interferon Regulatory Factor-2 is a Transcriptional Activator in Muscle where it Regulates Expression of Vascular Cell Adhesion Molecule-1," *The Journal of Cell Biology*, vol. 140, No. 5, pp. 1265-1276, 1998.

Shuji Ozaki et al. (1999) "Interferon-alpha and gamma enhance the HM1.24 Expression on Myeloma Cells Through the STAT-signaling Pathway," Blood 94(10), pp. 549a.

Supplementary Partial Search Report dated Oct. 26, 2005, directed to a corresponding foreign application.

Goto et al. (Sep. 15, 1994). "A Novel Membrane Antigen Selectively Expressed on Terminally Differentiated Human B Cells" *Blood.* 84(6): 1922-1930.

Kayo Inaba et al. "Contrasting Effect of $\alpha/\beta$- and $\gamma$-Interferons On Expression Of Macrophage Ia Antigens," Department of Zoology, Faculty of Science, and the Institute for Virus Research, Kyoto University, Kyoto, Japan, vol. 163, Apr. 1986, pp. 1030-1035.

Michele Maio et al. "Modulation by Interferons of HLA Antigen, High-Molecular-Weight Melanoma-associated Antigen, and Intercellular Adhesion Molecule 1 Expression by Cultured Melanoma Cells with Different Metastatic Potential," Cancer Research 49, Jun. 1, 1989, pp. 2980-2987.

Susan E. Dovhey et al. "Loss of Interferon-$\gamma$ Inducibility of TAP1 and LMP2 in a Renal Cell Carcinoma Cell Line," Cancer Research 60, Oct. 15, 2000, pp. 5789-5796.

Arora et al. (1998) Differential Myeloma Cell Responsiveness to Interferon-Alpha Correlates with Differential Induction of p19INK4d and Cyclin D2 Expression JBC 273(19), pp. 11799-11805.

Australian Office Action dated May 18, 2004.

Australian Office Action mailed Apr. 1, 2005, directed to counterpart foreign application.

Birnbaum et al., "Phosphorylation of the Oncogenic Transcription Factor Interferon Regulatory Factor 2 (IRF2) In Vitro and In Vivo", Journal of Cellular Biochemistry 66 (1997) pp. 175-183.

Bungard et al., (1998) "The Combination of IL-2 and IFN Alpha Effectively Augments the Antibody-Dependent Cellular Cytotoxicity of Monoclonal Antibodies 17-1A and BR 55-2 Against the Colorectal Carcinoma Cell Line HT29," Cancer Immun Immunothe 46, pp. 213-220.

Cha et al, "Human Interferon Regulatory Factor 2 Gene," *The Journal of Biological Chemistry*, vol. 269, No. 7, Feb. 18, 1994, pp. 5279-5287.

European Office Action mailed Oct. 21, 2005 directed to EP Application No. 00953561.8.

Ishikawa et al. "Molecular Cloning and Chromosomal Mapping of a Bone Marrow Stromal Cell Surface Gene, BST2, That May Be Involved in Pre-B-Cell Growth" A Stromal Cell Molecule Involved in Pre-B-Cell Growth, Cenomics 26, pp. 527-534, 1996.

Kosaka et al. "Advances in Understanding Biology and Pathogenesis of Multiple Myeloma" Japanese Clinical vol. 53, No. 3, Mar. 1995, pp. 627-635.

Langer et al. "Interferon Receptors" Immunology Today, vol. 9, No. 12, 1988, pp. 393-400.

Lengyel "Tumor-suppressor Genes: News About the Interferon Connection" Proc. Natl. Acad. Sci. USA, vol. 90, pp. 5893-5895, Jul. 1993.

Ludwig et al. "Current Controversies in Cancer—Should Alpha-interferon be Included as Standard Treatment in Multiple Myeloma?" European Journal of Cancer, vol. 34, No. 11, pp. 12-24, 1998.

Mellstedt et al. (Oct. 1991) "Treatment of Multiple Myeloma with Interferon Alpha: the Scandinavian Experience," Br J Haernatol vol. 79, Supp 1, pp. 21-25.

Office Action Report from European Patent Office dated Apr. 6, 2004.

Ozaki et al. (1997) "Immunotherapy of Multiple Myeloma with a Monoclonal Antibody Directed Against a Plasma Cell-Specific Antigen, HM1.24" *Blood* 90(8), pp. 3179-3186.

Pestka et al. "Interferons and Their Actions" Am. Rev. Biochem. vol. 56, 1987, pp. 727-777.

Platanias, Leonidas C., et al. "Signaling Pathways Activated by Interferons," Experimental Hematology 27 (1999) pp. 1583-1592.

*The Merck Index* (12$^{th}$ Ed.) Merck & Co., Inc., 1996, pp. 856-857, entries 5016 and 5018.

US Office Action directed U.S. Appl. No. 10/069,290 mailed Oct. 6, 2004 (7 pages).

US Office Action directed to U.S. Appl. No. 10/069,290 mailed Feb. 4, 2005 (9 pages).

US Office Action directed to U.S. Appl. No. 10/069,290 mailed Oct. 14, 2005 (7 pages).

US Office Action directed to U.S. Appl. No. 11/402,927 mailed Apr. 29, 2008 (14 pages).

US Office Action directed to U.S. Appl. No. 11/402,927 mailed Feb. 17, 2009 (8 pages).

Verharr, M., et al., "In Vitro Upregulation Of Carcinoembryonic Antigen Expression By Combinations Of Cytokines" Cancer Lett., (May 1999), vol. 139, No. 1., pp. 67-73.

Wiklund et al. (1991) "Recombinant Interferon-$\gamma$ Inhibits the Growth of IL-6 Dependent Human Multiple Myeloma Cell Lines in Vitro," Eur J Haematol vol. 46, pp. 231-239.

International Search Report mailed on Nov. 21, 2000, directed to International Patent Application No. PCT/JP00/05617; 4 pages.

International Search Report mailed on May 21, 2002, directed to International Patent Application No. PCT/JP02/00989; 8 pages.

Kosaka, M. et al. US Office Action directed towards U.S. Appl. No. 11/402,927 mailed Jan. 7, 2010; 9 pages.

Muralikrishna, K. et al., (1997) "Differential modulation of LAK and ADCC functions of natural killer cells from AK-5 tumor-bearing rats by IL-2, IL-12 and IFN-$\gamma$" *Cytokine, Cellular & Molecular Therapy* vol. 3:51-58.

Sung, M. et al., (1996) "Protective effects of interferon-$\gamma$ on squamous-cell carcinoma of head and neck targets in antibody-dependent cellular cytotoxicity mediated by human natural killer cells" *Int. J. Cancer* vol. 66:393-399.

Kosaka, Masaaki et al. (1995). "Advances in Biology and Pathogenesis of Multiple Myeloma," *The First Department of Internal Medicine, School of Medicine, The University of Tokushima* 53:627-635.

Ozaki, Shuji et al. (1999). "Humanized Anti-HM1.24 Antibody Mediates Myeloma Cell Cytotoxicity That is Enhanced by Cytokine Stimulation of Effector Cells,"*Blood* 93(11):3922-3930.

Tokyo Kagaku Dojin Co., Ltd.(1990). "Interferon Cytokine", *Toshiaki Osawa etd.*:115-135.

Hashimoto-Gotch, Tamotsu et al. (1995). "An Oligodeoxyribonucleotide-directed dual amber method for site-directed Mutagenesis," *Gene*:152:271-275.

Zoller, Mark J. et al.(1983). "Oligonucleotide-Directed Mutagenesis of DNA Fragments Cloned into M13 Vectors, " *Methods in Enzymology* 100:468-500.

Kramer, Wilfried et al. (1984). "The Gapped Duplex DNA Approach to Oligonucleotide-directed Mutation Construction, "*Nucleic Acids Research* 12(24):9441-0456.

Kunkel, Thomas A. (1985). "Rapid and Efficient Site-specific Mutagenesis without Phenotypic Selection," *Proc. Natl. Acad. Sci. USA.* 82:488-492.

New Cell Engineering Experimental Protocol edited by Dept. of Oncology, Inst. of Medical Science, Univ. Of Tokyo (1993). pp. 241-248.

Mark, D.F. et al. (1984). "Site-specific Mutagenesis of the Human Fibroblast Interferon Gene," *Proc. Natl. Acad. Sci. USA.* 81:5662-5666.

Itoh, Susuma et al. (1989). "Sequence of a cDNA coding for Human IRF-2," *Nucleic Acids Research* 17(20):8372.

Harada, Hisashi et al. (1989). "Structurally similar but Functionally Distinct Factors, IRF-1 and IRF-2, Bind to the Same Regulatory Elements of IFN and IFN-Inducible Genes," *Cell* 58:729-739.

Goto, T. et al. (1991). "Establishment of Myeloma Cell Line (KPC-32) and Production of Monoclonal Antibody that Recognizes Cell Surface Antigen," *Japan J. Clin. Hematol.* 32:1400.

Kearney, John F. et al. (1979). "A new Mouse Myeloma Cell Line that has Lost Immunoglobulin Expression but Permits the Construction of Antibody-Secreting Hybrid Cell Lines," *The Journal of Immunology* 123(4):1548-1550.

Yelton, D.E. (1978). "Fusion of Mouse Myelom and Spleen Cells," *Current Topics in Microbiology and Immunology* 81:1-7.

Kohler, G. et al. (1976). "Derivation of Specific Antibody-producing Tissue Culture and Tumor Lines by Cell Fusion," *Eur. J. Immunol.* 6:511-519.

Margulies, David H. (1976). "Somatic Cell Hybridization of Mouse Myeloma Cells," *Cell* 8:405-415.

Shulman, M. et al. (1978). "A Better Cell Line for Making Hybridomas Secreting Specific Antibodies," *Nature* 276:269-270.

De St. Groth, S.F. et al. (1980). "Production of Monoclonal Antibodies: Strategy and Tactics," *Journal of Immunological Methods* 35:1-21.

Trowbridge, Ian S. (1978). "Interspecies Spleen-Myeloma Hybrid Producing Monoclonal Antibodies Against Mouse Lymphocyte Surface Glycoprotein, T200," *J. Exp. Med.* 148:313-323.

Galfre, G. et al. (1979). "Rat x Rat Hybrid Myelomas and a Monoclonal Anti-Fd Portion of Mouse IgG," *Nature* 277:131-133.

Galfre, G. et al. (1981). "Preparation of Monoclonal Antibodies: Strategies and Procedures," *Methods in Enzymology* 73:3-46.

Chirgwin, J.M. et al. (1979). "Isolation of Biologically Active Ribonucleic Acid from Sources Enriched in Ribonuclease," *Biochemistry* 18:5294-5299.

Chomczynski, P. et al. (1987). "Single-Step Method of RNA Isolation by Acid Guanidinium Thiocyanate-Phenol-Chloroform Extraction," *Analytical Biochemistry* 162:156-159.

Frohman, Michael A. et al. (1988). "Rapid Production of Full-Length cDNAs from Rare Transcripts: Amplification Using a Single Gene-Specific Oligonucleotide Primer," *Proc. Natl. Acad. Sci. USA*, 85: 8998-9002.

Belyaysky, A. et al. (1989). "PCR-based CDNA Library Construction: General cDNA Libraries at the Level of a few Cells," *Nucleic Acids Research* 17(8):2919-2932.

Sato, K. et al. (1993). "Reshaping a Human Antibody to Inhibit the Interleukin 6-Dependent Tumor Cell Growth," 9*Cancer Research* 53:851-856.

Mulligan, Richard C. (1979). "Synthesis of Rabbit β-globin in Cultured Monkey Kindney Cells Following infection with a SV40 β-globin Recombinant Genome," *Nature* 277:108-114.

Mizushima, S. et al. (1990). "pEF-BOS, a Powerful Mammalian Expression Vector," *Nucleic Acids Research* 18 (17):5322.

Ward, E.S. et al. (1989). "Binding Activities of a Repertoire of Single Immunoglobulin Variable Domains Secreted from *Escherichia coli*" *Nature* 341: 544-546.

Ward, E.S. (1992). "Antibody Engineering: the Use of *Escherichia coli* as an Expression Host,"*Faseb J.* 6:2422-2427.

Better, M. et al. (1988). "*Escherichia coli* Secretion of an Active Chimeric Antibody Fragment," *Sciencei* 2210:1041-1043.

Lei, S. P. et al. (1987). "Characterization of the *Erwinia Carotovora* pelB Gene and its Product Pectate Lyase," *Journal of Bacteriology*, 169: 4379-4383.

Ebert, K. M. (1994). "Induction of Human Tissue Plasminogen Activator in the Mammary Gland of Transgenic Goats," *Bio/Technology* 12:699-702.

Maeda, S. et al. (1985). "Production of Human α-interferon in Silkworm using a Baculovirus Vector," *Nature* 315:592-594.

Ma, J. K-C. et al. (1994). "Assembly of Monoclonal Antibodies with IgG1 and IgA Heavy Chain Domains in Transgenic Tobacco Plants," *Eur. J. Immunol.* 24:131-138.

Smith, R.I.F. et al. (1994). "Recombinant Plymeric IgG: An Approach to Engineering More Potent Antibodies," *Bio/Technology* 12:683-688.

Smith, R.I.F et al. (1995). "Addition of a µ-Tailpiece to IgG Results in Polymeric Antibodies with Enhanced Effector Functions Including Complement-Mediated Cytolysis by IgG4," *The Journal of Immunology* 154:2226-2236.

Shuford, W. et al. (1991). "Effect of Light Chain V Region Duplication on IgG Oligomerization and in Vivo Efficacy," *Science* 252:724-727.

Caron, P.C. et al. (1992). "Engineered Humanized Dimeric Forms of IgG Are More Effective Antibodies," *J. Exp. Med.* 176:1191-1195.

Shopes, B. (1992). "A Genetically Engineered Human IgG Mutant with Enhanced Cytolytic Activity," *The Journal of Immunology* 148:2918-2922.

Wolff, E.A. (1993). "Monoclonal Antibody Homodimers: Enhanced Antitumor Activity in Nude Mice," *Cancer Research* 53:2560-2565.

Norderhaug, L. et al. (1991). "Chimeric Mouse Human IgG3 Antibodies with an IgG4-like Hinge Region Induce Complement-mediated Lysis more Efficiently than IgG3 with Normal Hinge," *Eur. J. Immunol.* 21:2379-2384.

Clark. (1993) "Protein Engineering of Antibody Molecules for Prophylactic and Therapeutic Applications in Man", pp. 1; cover page.

Eisenthal et al. (1989) "Systemic Induction of Cells Mediating Antibody-dependent Cellular Cytotoxicity Following Administration of Interleukin 2", *Cancer Research*, Dec. 15, 1989, vol. 49, pp. 6953-6959.

Evans et al., (Jul. 10, 1997) "IL-15 Mediates Anti-Tumor Effects After Cyclophosphamide Injection of Tumor-bearing Mice and Enhances Adoptive Immunotheraphy: The Potential Role of NK Cell Subpopulations." *Cellular Immunology*, 179:66-73 (Abstract only).

Gill et al., (Oct. 1, 1989) "Synergistic Antitumor Effects of Interleukin 2 and the Monoclonal Lym-1 Against Human Burkitt Lymphoma Cells in Vitro and in Vivo," *Cancer Research* 49:5377-5379.

Hanton et al. (1984) The Reaction of Antibody-Dependent Cell Mediated Cytotoxicity (ADCC). "*Annales de Recherches Veterinaires*" 15(4):443-454. (English translation of Abstract).

Hird et al. (1990). "Immunotheraphy with Monoclonal Antibodies." *Genes and Cancer*, (Monograph). 183-189 and cover page.

Kay, Neil K. (1987) "Restoration of Impaired Natural Killer Cell Activity of B-Chronic Lymphocytic Leukemia Patients by Recombinant Interleukin-2", *American Journal of Hematology*: 24(2):161-167.

Kosaka et al., U.S. Office Action mailed Feb. 24, 2006, directed towards U.S. Appl. No. 10/428,085; 10 pages.

Kosaka et al., U.S. Office Action mailed Nov. 21, 2006, directed towards U.S. Appl. No. 10/428,085; 11 pages.

Kosaka et al., U.S. Office Action mailed Sep. 6, 2007, directed towards U.S. Appl. No. 10/428,085; 8 pages.

Kosaka et al., U.S. Office Action mailed Jun. 11, 2008, directed towards U.S. Appl. No. 10/428,085; 7 pages.

Kosaka et al., U.S. Office Action mailed Mar. 5, 2009, directed towards U.S. Appl. No. 10/428,085; 4 pages.

Kosaka, M. et al. US Office Action directed towards U.S. Appl. No. 11/402,927 mailed Jul. 20, 2010; 10 pages.

Mihich et al. (1986) "Future Perspectives for Biological Response Modifiers: A View Point." *Seminars in Oncology*. 13(2):234-254.

Ottonello et al. (Jun. 15, 1996) "Monoclonal Lym-1 Antibody-Dependent Lysis of B-Lymphoblastoid Tumor Targets by Human Complement and Cytokine-Exposed Monocuclear and Neutrophilic Polymorphonuclear Luekocytes." *Blood*. 87(12):5171-5178.

Ozaki et al. (1996) "Localization and Imaging of Human Plasmacytoma Xenografts in Severe Combined Immunodeficiency Mice by a New Murine Monoclonal Antibody, Anti-HM1.24," *Tokushima J. Exp. Med.* 43:7-15.

Parkinson, David R. (Dec. 29, 1995) "Present Status of Biological Response Modifiers in Cancer", *American Journal of Medicine*, 99(6A):54S-56S.

Pawelec et al. (1989) "Partial Correction of Defective Generation of Lymphokine-Activated Killer Cells in Patients with Chronic Myelogenous Leukemia After in vivo Treatment with Interferon-α (Wellferon)", *Cancer Immunology Immunotherapy*. 29(1): 63-66.

Peest et al. (1995) "Low Dose Recombinant Interleukin-2 Therapy in Advanced Multiple Myeloma", *British Journal of Haematology*. 89(2):328-337.

Schlom, J. (1991) "Monoclonal Antibodies; They're More and Less Than You Think", *Molecular Foundations of Oncology*. 95-134 and cover page.

Stewart et al. (1997) "Immunogene Therapy with Interleukin 12 (IL-12), B7-1 and Flt3 Ligand (FIt3L) in a Murine Myeloma Model: IL-12 and B7-1 Expressing Cells Confer Protective Immunity", *Blood*, vol. 90(10) Suppl1, Part 1: 358A-359A.

Takeuchi et al. (Dec. 1996) "Induction by Interleukin-15 of Human Killer Cell Activity Against Lung Cancer Cell Lines and Its Regulatory Mechanisms." *Japanese Journal of Cancer Research*. 87(12):1251-1258 (Abstract only).

Vachino et al. (Nov. 15, 1991) "Complement Activation in Cancer Patients Undergoing Immunotherapy With Interleukin-2 (IL-2): Binding of Complement and C-Reactive Protein by IL-2-Activated Lymphocytes", *Blood*, 78(10):2505-2513.

\* cited by examiner

Fig.1
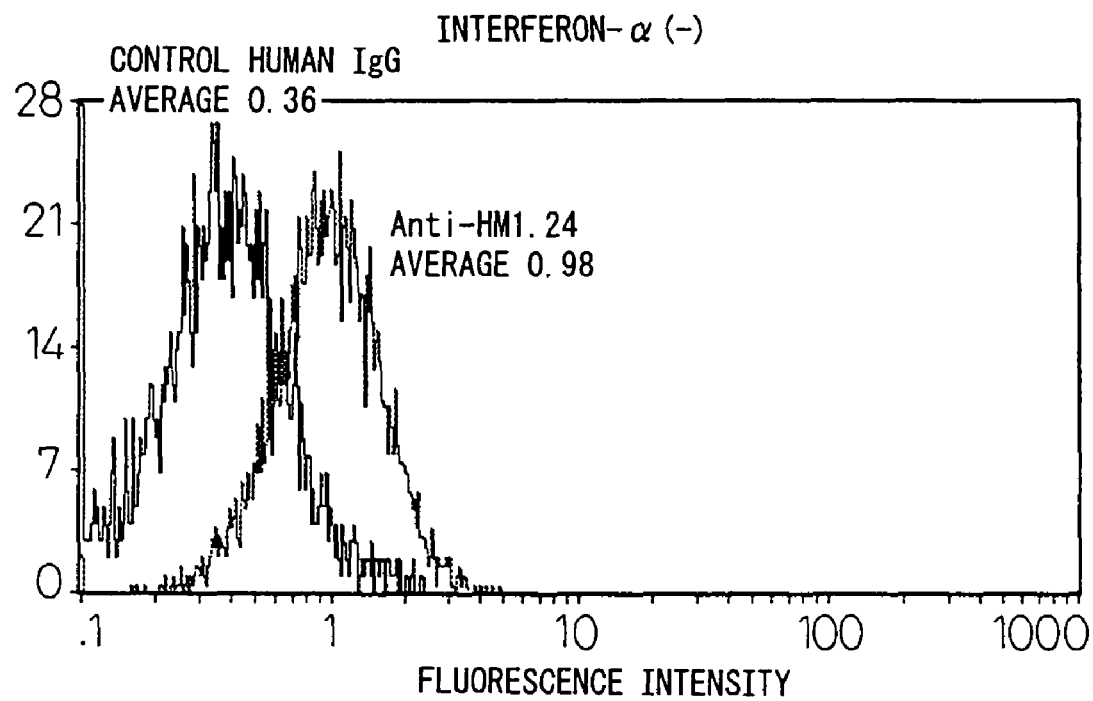
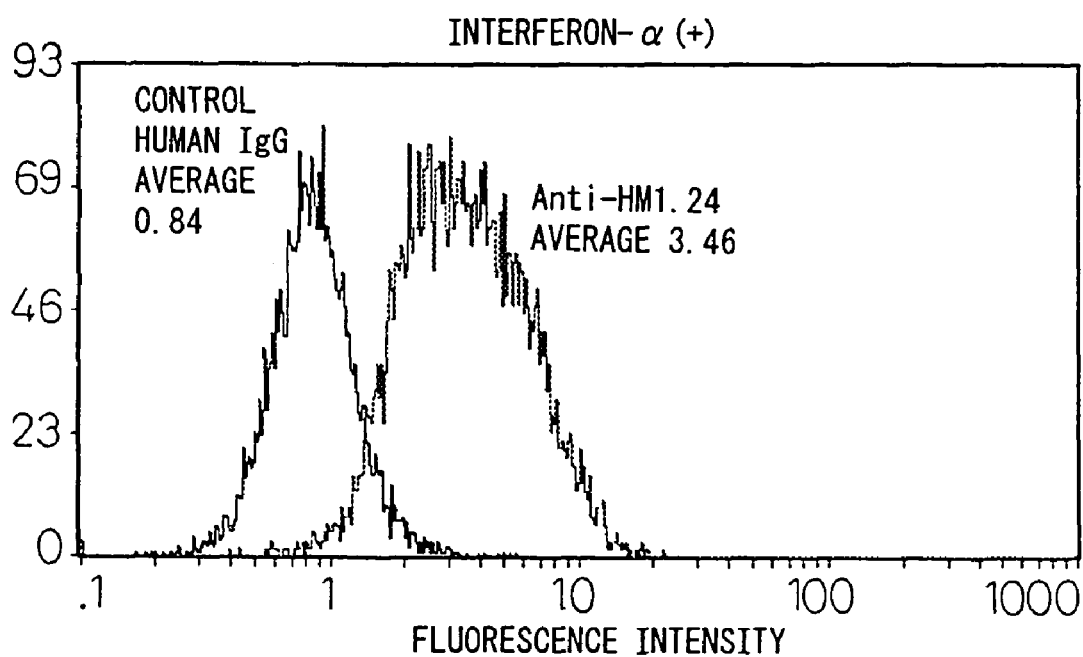

Fig.2
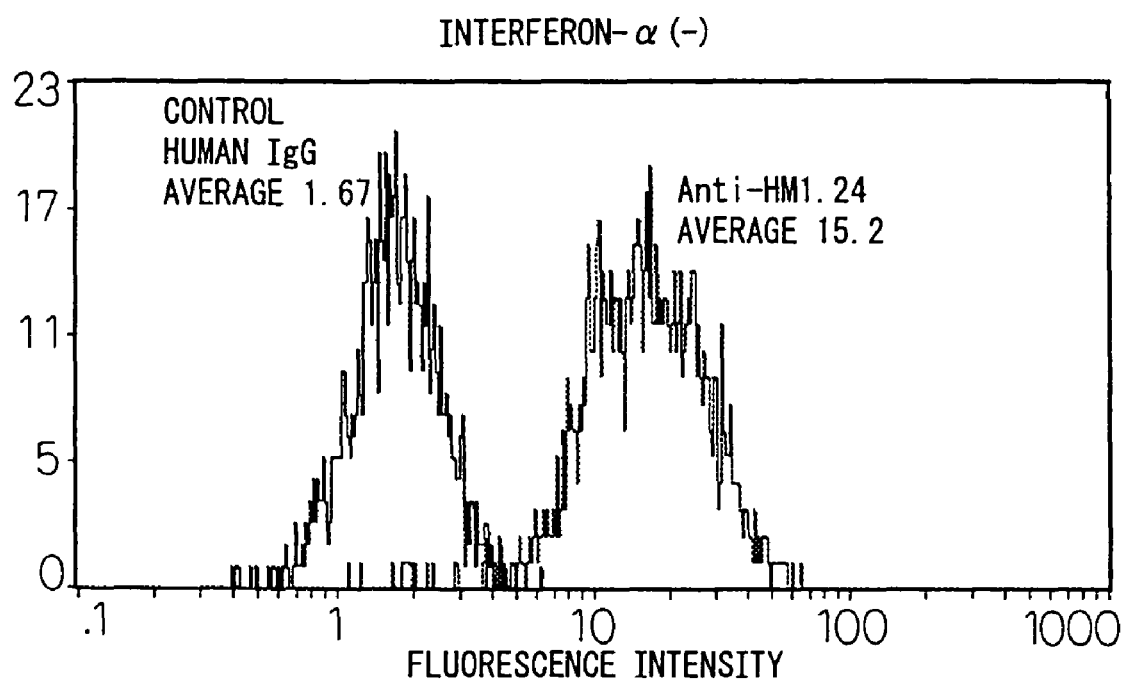
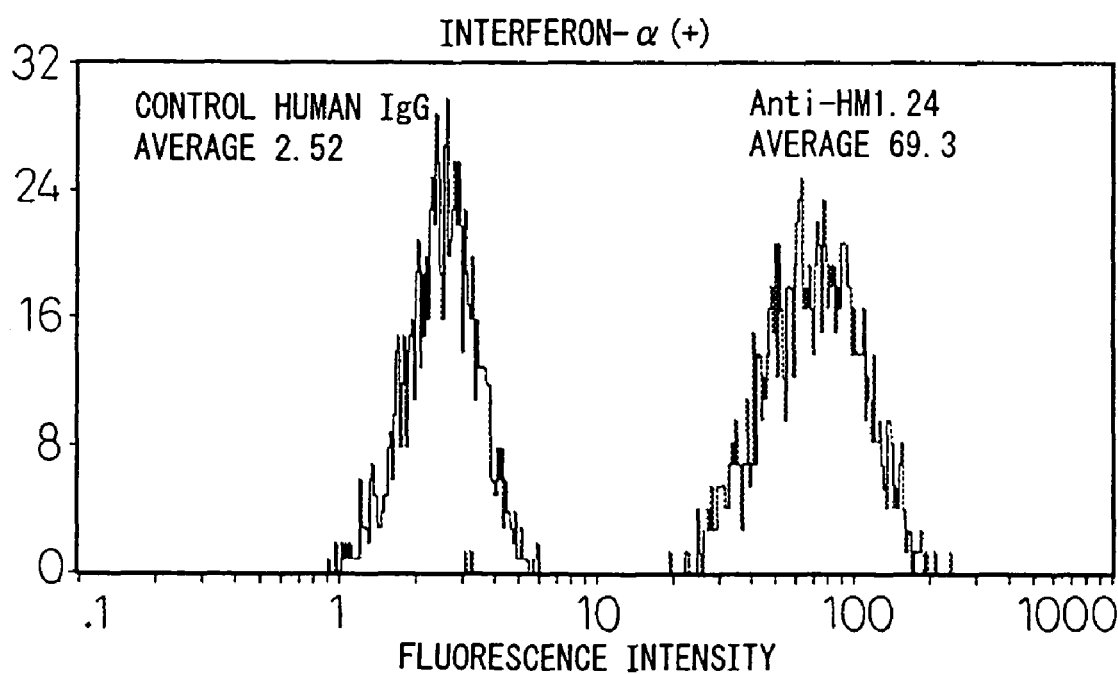

Fig.5
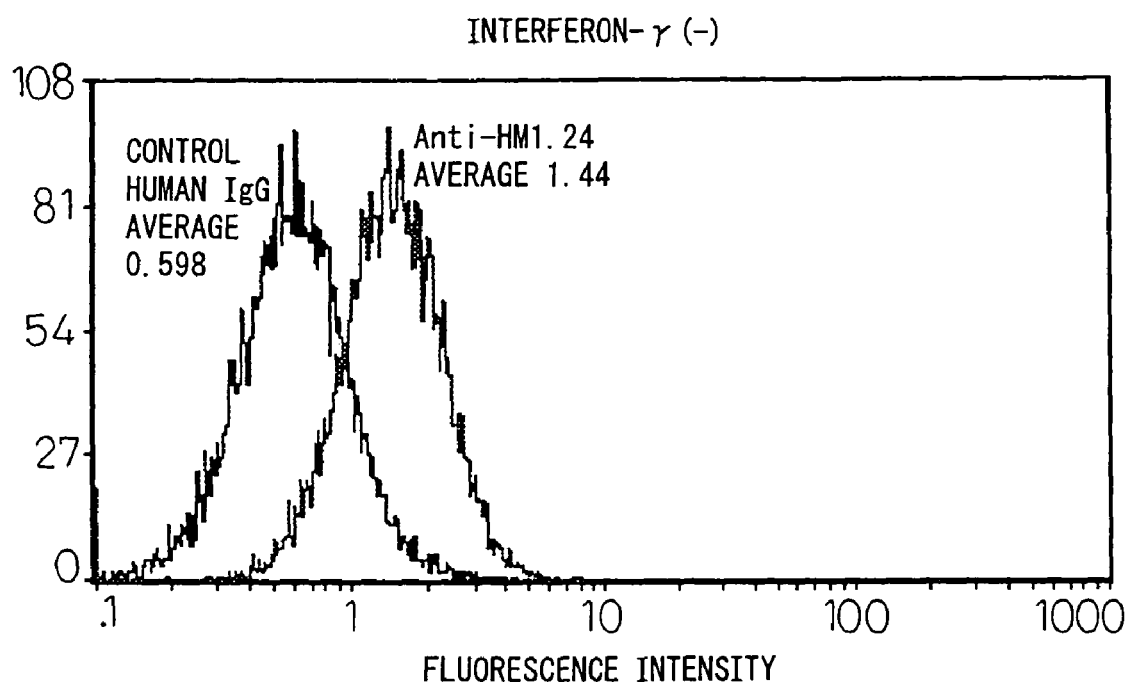
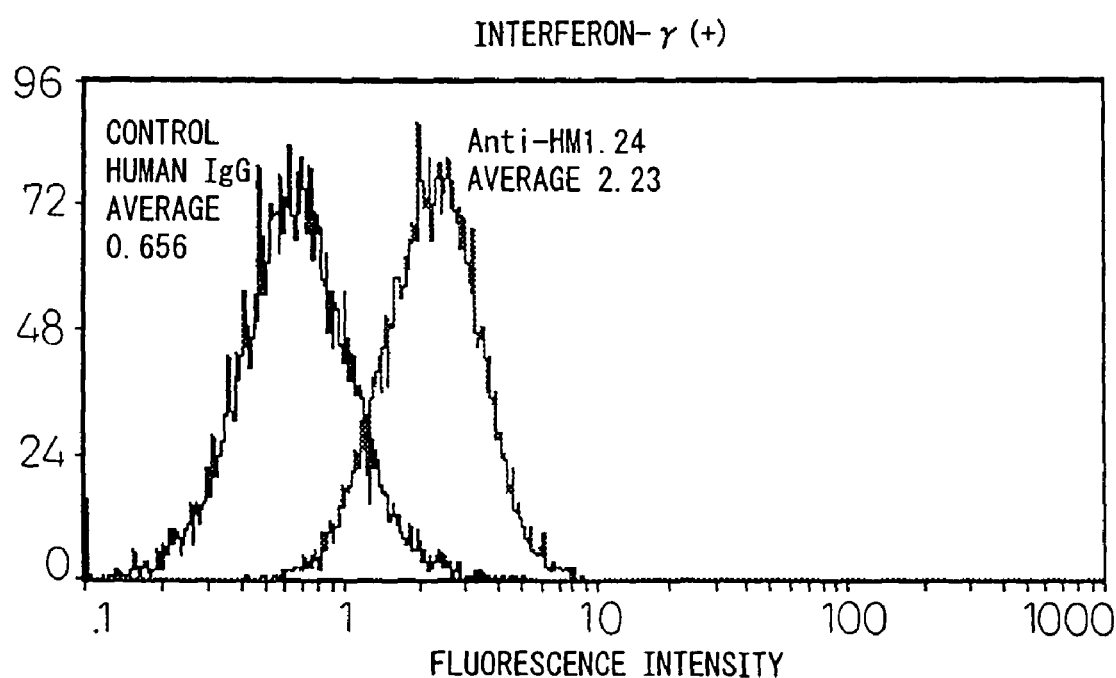

Fig.6
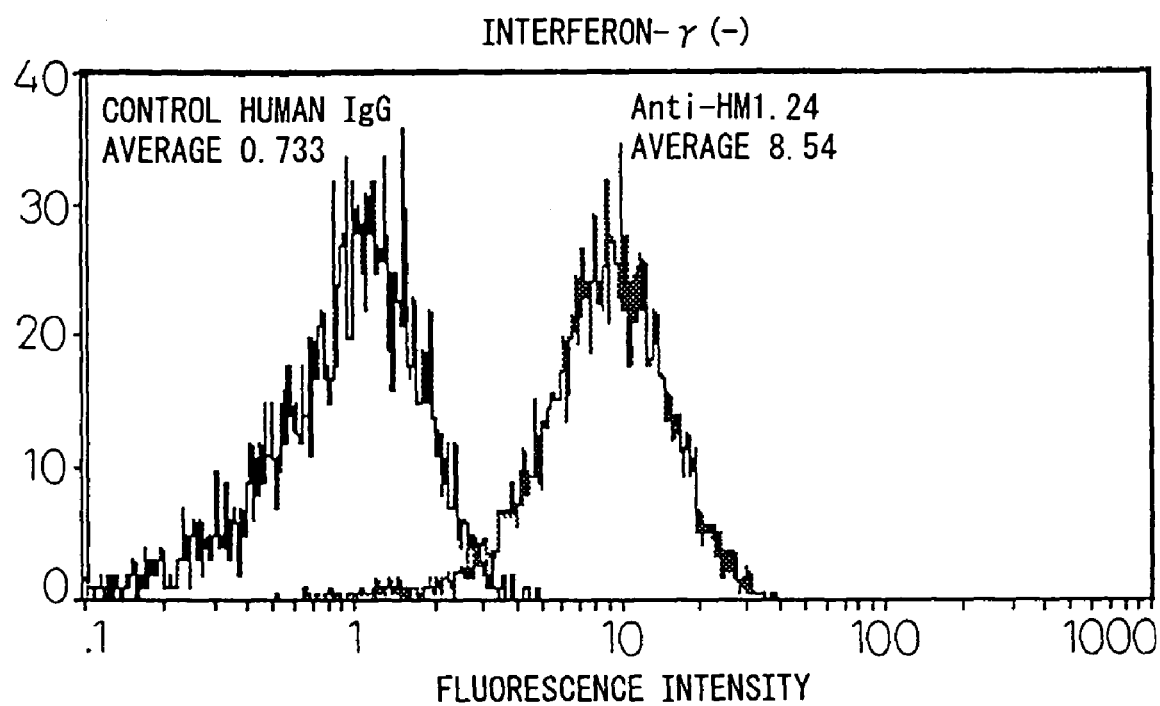
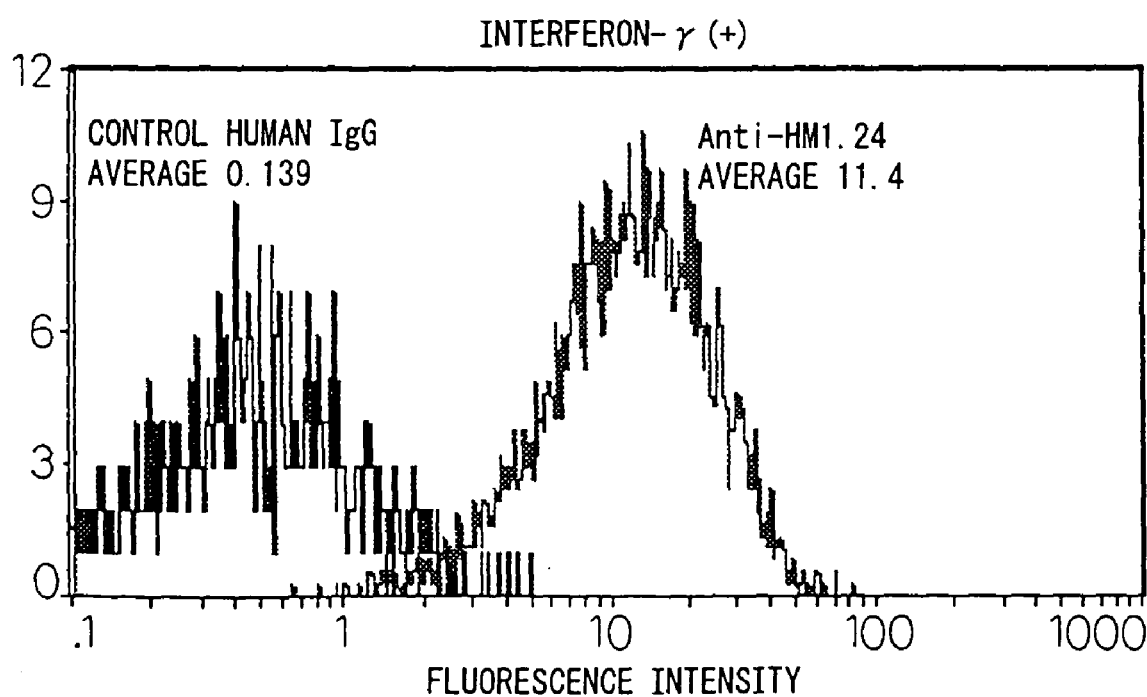

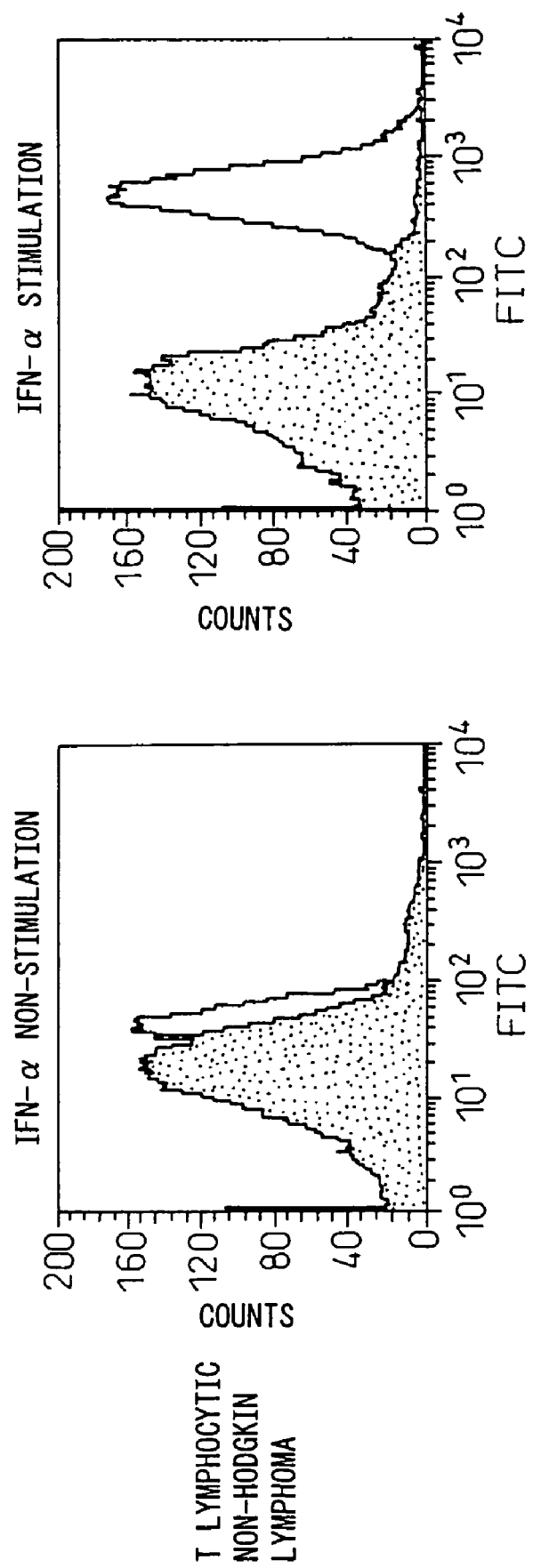

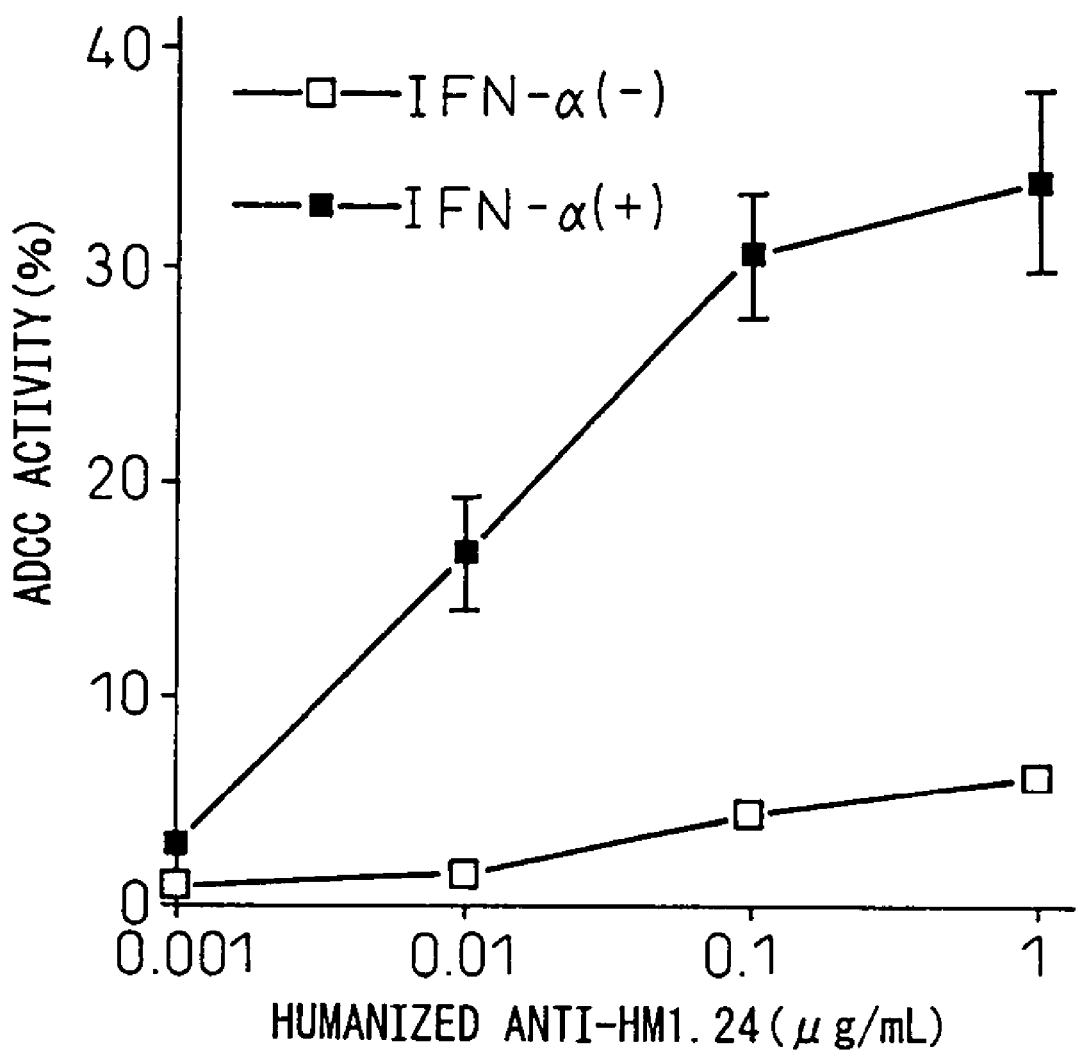

SEQUENCE LISTING

<160> NUMBER OF SEQ ID NOS: 25

<210> SEQ ID NO 1
<211> LENGTH: 1013
<212> TYPE: DNA
<213> ORGANISM: Homo sapiens
<220> FEATURE:
<223> OTHER INFORMATION: Nucleotide sequence coding for HM1.24 protein antigen

<400> SEQUENCE: 1

```
gaattcggca cgagggatct gg atg gca tct act tcg tat gac tat tgc            49
                         Met Ala Ser Thr Ser Tyr Asp Tyr Cys
                          1               5 aga gtg ccc atg gaa gac ggg gat aag cgc tgt aag ctt ctg ctg ggg         97
Arg Val Pro Met Glu Asp Gly Asp Lys Arg Cys Lys Leu Leu Leu Gly
 10              15                  20                  25 ata gga att ctg gtg ctc ctg atc atc gtg att ctg ggg gtg ccc ttg        145
Ile Gly Ile Leu Val Leu Leu Ile Ile Val Ile Leu Gly Val Pro Leu
                 30                  35                  40 att atc ttc acc atc aag gcc aac agc gag gcc tgc cgg gac ggc ctt        193
Ile Ile Phe Thr Ile Lys Ala Asn Ser Glu Ala Cys Arg Asp Gly Leu
                 45                  50                  55 cgg gca gtg atg gag tgt cgc aat gtc acc cat ctc ctg caa caa gag        241
Arg Ala Val Met Glu Cys Arg Asn Val Thr His Leu Leu Gln Gln Glu
             60                  65                  70 ctg acc gag gcc cag aag ggc ttt cag gat gtg gag gcc cag gcc gcc        289
Leu Thr Glu Ala Gln Lys Gly Phe Gln Asp Val Glu Ala Gln Ala Ala
     75                  80                  85 acc tgc aac cac act gtg atg gcc cta atg gct tcc ctg gat gca gag        337
Thr Cys Asn His Thr Val Met Ala Leu Met Ala Ser Leu Asp Ala Glu
 90                  95                 100                 105 aag gcc caa gga caa aag aaa gtg gag gag ctt gag gga gag atc act        385
Lys Ala Gln Gly Gln Lys Lys Val Glu Glu Leu Glu Gly Glu Ile Thr
                110                 115                 120 aca tta aac cat aag ctt cag gac gcg tct gca gag gtg gag cga ctg        433
Thr Leu Asn His Lys Leu Gln Asp Ala Ser Ala Glu Val Glu Arg Leu
                125                 130                 135 aga aga gaa aac cag gtc tta agc gtg aga atc gcg gac aag aag tac        481
Arg Arg Glu Asn Gln Val Leu Ser Val Arg Ile Ala Asp Lys Lys Tyr
            140                 145                 150 tac ccc agc tcc cag gac tcc agc tcc gct gcg gcg ccc cag ctg ctg        529
Tyr Pro Ser Ser Gln Asp Ser Ser Ser Ala Ala Ala Pro Gln Leu Leu
155                 160                 165 att gtg ctg ctg ggc ctc agc gct ctg ctg cag tga gatcccagga            575
Ile Val Leu Leu Gly Leu Ser Ala Leu Leu Gln
170                 175                 180 agctggcaca tcttggaagg tccgtcctgc tcggcttttc gcttgaacat tcccttgatc     635
tcatcagttc tgagcgggtc atgggcaac acggttagcg gggagagcac ggggtagccg      695
```

```
gagaagggcc tctggagcag gtctggaggg gccatggggc agtcctgggt ctggggacac      755
agtcgggttg acccagggct gtctccctcc agagcctccc tccggacaat gagtcccccc      815
tcttgtctcc caccctgaga ttgggcatgg ggtgcggtgt ggggggcatg tgctgcctgt      875
tgttatgggt ttttttttgcg ggggggttg cttttttctg ggtctttga gctccaaaaa      935 aataaacact tcctttgagg gagagcacac cttaaaaaaa aaaaaaaaa aaaaaaaaa        995 aaaattcggg cggccgcc                                                   1013

<210> SEQ ID NO 2
<211> LENGTH: 180
<212> TYPE: PRT
<213> ORGANISM: Homo sapiens
<220> FEATURE:
<223> OTHER INFORMATION: Amino acid sequence of HM1.24 protein antigen

<400> SEQUENCE: 2

Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Leu Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180

<210> SEQ ID NO 3
<211> LENGTH: 2061
<212> TYPE: DNA
<213> ORGANISM: Homo sapiens
<220> FEATURE:
<223> OTHER INFORMATION: Nucleotide sequence of promoter region of gene
      coding for HM1.24 protein antigen

<400> SEQUENCE: 3
actaaaagtc tctgatatgc agaaataatg gcataagctg tctttctgtc tgtcccctct       60
ctctctctct gcctcggctg ccaggcaggg aagggccccc tgtccagtgg acacgtgacc      120
cacatgacct tacctatcat tggagatgac tcacactctt taccctgccc cttttgcttt      180
gtatccaata ataacagca cagccagaca ttcggggcca ctaccagtct ccgcgcattg       240
ctggtagtgg tccccggggc ccagctgtct tttcttttat ctcttcgtct tgtgtcttta     300
tttctacact ctctcgtcgc cgcacacagg gagagaccca ctgaccctgt ggggctggtc      360
```

```
cctacagtaa ttttaaaggg aagagcaaca aactttcggt ttgcaggggct gggactgttt    420
acagctgcaa aatttagaga ggacatcaat ctattattat ccacatttta cagctgggga    480
aatcaatgct aagagaggaa attcatttgc ccagaggtgc accaccctgg cctccaatgt    540
gcaattcatg caattgtgat ttccgacctg gtcccaaact aaccctaaag ttagcaggcc    600
agaacagtgc tgctcaaata agtcagctta gtcaaataag tcaggcaaag gtcgtgtctt    660
tgcacctgga gtcctggcca ggctggtagg tccctcctcc tgggacaagt tcaccctcag    720
aattttcagc aagatcatct cccacagctt gttaattggt tcttggttct aagtgatttt    780
tttgtttatt ggtttaagag atgggatccc actctatcac ccaggcttga gtgccgtggc    840
acaatcatag ctcgctgcag cctcaaactc ctgggctcga gtgatcctcc tgcctcagcc    900
tcccagcctc agcctgggac acaggcatg taccaccatg cctggctcta agtggcttta    960
atggggtcct tctgagggat gttggagtca gggcctgggg ggagttcccc aggccttctg    1020
ggaggcctgg gctctggact tgacctcgcc tactgtctgg ccctgctgaa aagaaaaaaa    1080
aacatggaaa tggcagacct aacagaatct gggctgtggt caggatgtgg ctgaagaagc    1140
cacaagaaaa acatgcagtc cccttttcagc ggtcatgccc agcagttggg tgccgataat    1200
gggcctgatt tcctgtagga agccctggct ctcttggcca catggacagt gtctgaggct    1260
ggccctgtta ttcccctttg cagatgaaga aacaggctca gagagtttac ctggtatcct    1320
ggagtcccag gagcactttt tctggaagta ggagcttgtt tcctgcaggt gccaagacag    1380
agaccgacat tgtttgttgg ctgggtcggt ctcccagttt tcagctggct ccagtctcac    1440
ctgttgctca cacaccctcc atgtctccca tagtcccctc ggtggggaca gaggcactgg    1500
atgaagccct gctcgtcacc acagagacac ctgaacacaa aaaccagtcc ctggggtcag    1560
acccaggccc cgcccccaga cccaggccct gccctcactc caccacgcaa ctgtgcaacc    1620
tcagttttccc caggtggaga ccggaccaac aatgatggcc tctgcctctt caggtcatag    1680
tacagatgaa tacaggctgg cacggcctag gcactcagta acacacggca gaggcacagg    1740
gacttaagat ggagtgtccc aggcagccac agttggctgg cacccagttg ggaagggccc    1800
aagggctttt aaagcagggt gaaaaaaaaa gcccacctcc tttctgggaa actgaaactg    1860
aaaacctaat taatcctctg cctgtaggtg cctcatgcaa gagctgctgg tcagagcact    1920
tcctggaact tgctattggt caggacgttt cctatgctaa taaaggggtg gcccgtagaa    1980
gattccagca ccctcccctta actccaggcc agactccttt cagctaaagg ggagatctgg    2040
atg gca tct act tcg tat gac                                        2061

<210> SEQ ID NO 4
<211> LENGTH: 29
<212> TYPE: DNA
<213> ORGANISM: Artificial Sequence
<220> FEATURE:
<223> OTHER INFORMATION: Primer HM2K

<400> SEQUENCE: 4
aaaggtacca gctgtctttc tgtctgtcc                                       29

<210> SEQ ID NO 5
<211> LENGTH: 28
<212> TYPE: DNA
<213> ORGANISM: Artificial Sequence
<220> FEATURE:
<223> OTHER INFORMATION: Primer BST2B

<400> SEQUENCE: 5
```

```
atagtcatac gaagtagatg ccatccag                                      28

<210> SEQ ID NO 6
<211> LENGTH: 2144
<212> TYPE: DNA
<213> ORGANISM: Homo sapiens
<220> FEATURE:
<223> OTHER INFORMATION: Nucleotide sequence coding for IRF-2 protein

<400> SEQUENCE: 6
aactgacggg ctttcatttc catttcacac accctagcaa cacttatacc ttgcggaatt    60
gtattggtag cgtgaaaaaa gcacactgag agggcaccat gccggtggaa aggatgcgca   120
tgcgcccgtg gctggaggag cagataaact ccaacacgat cccggggctc aagtggctta   180
acaaggaaaa gaagattttt cagatcccct ggatgcatgc ggctagacat gggtgggatg   240
tggaaaaga tgcaccactc tttagaaacc gggcaatcca tacaggaaag catcaaccag    300
gagtagataa acctgatccc aaaacatgga aggcgaattt cagatgcgcc atgaattcct   360
tgcctgatat tgaagaagtc aaggataaaa gcataaagaa aggaaataat gccttcaggg   420
tctaccgaat gctgccccta tcagaacggc cttctaagaa aggaagaaa ccaaagacag    480
aaaaagaaga caaagttaag cacatcaagc aagaaccagt tgagtcatct ctggggctta   540
gtaatggagt aagtgatctt tctcctgagt atgcggtcct gacttcaact ataaaaaatg   600
aagtggatag tacggtgaac atcatagttg taggacagtc ccatctggac agcaacattg   660
agaatcaaga gattgtcacc aatccgccag acatttgcca agttgtagag gtgaccactg   720
agagcgacga gcagccggtc agcatgagcg agctctaccc tctgcagatc tcccccgtgt   780
cttcctatgc agaaagcgaa acgactgata gtgtgcccag cgatgaagag agtgccgagg   840
ggcggccaca ctggcggaag aggaatattg aaggcaaaca gtacctcagc aacatgggga   900
ctcgaggctc ctacctgctg cccggcatgg cgtccttcgt cacttccaac aaaccggacc   960
tccaggtcac catcaaagag gagagcaatc cggtgcctta caacagctcc tggccccctt  1020
ttcaagacct cccccttct tcctccatga ccccagcatc cagcagcagt cggccagacc   1080
gggagacccg ggccagcgtc atcaagaaaa catcggatat cacccaggcc cgcgtcaaga   1140
gctgttaagc ctctgactct ccgcggtggt tgtgggggct tcttggcttt gttttgttgt   1200
ttgtttgtat tttattttt tctctctgac acctatttta gacaaatcta agggaaaag    1260
ccttgacaat agaacattga ttgctgtgtc caactccagt acctggagct tctcttaac    1320
tcaggactcc agcccattgg tagacgtgtg tttctagagc ctgctggatc tcccagggct   1380
actcactcaa gttcaaggac caacaagggc agtggaggtg ctgcattgcc tgcggtcaag   1440
gccagcaagg tggagtggat gcctcagaac ggacgagata atgtgaacta gctggaattt   1500
tttattcttg tgaatatgta cataggcagc actagcgaca ttgcagtctg cttctgcacc   1560
ttatcttaaa gcacttacag ataggccttc ttgtgatctt gctctatctc acagcacact   1620
cagcaccccc ttctctgccc attccccagc ctctcttcct atccatccc atccatccc    1680
atcccatccc atcccatccc gctctttcc tactttcct tccctcaaag cttccattcc    1740
acatccggag gagaagaagg aaatgaattt ctctacagat gtcccatttt cagactgctt   1800
taaaaaaat ccttctaatc tgctatgctt gaatgccacg cggtacaaag gaaaaagtat    1860
catggaaata ttatgcaaat tcccagattt gaagacaaaa atactctaat tctaaccaga   1920
gcaagctttt ttatttttta tacagggggaa tattttattc aaggtaaaat tctaaataaa   1980
atataattgt tttttatctt ttctacagca aatttataat tttaagattc ctttctttgt   2040
```
ttatcagcag ttgttattac atccttgtgg cacattttt tttaatttg taaaggtgaa    2100 aaaagctttt atgagctcat ctagcaatca gattttcctg tgga    2144

<210> SEQ ID NO 7
<211> LENGTH: 349
<212> TYPE: PRT
<213> ORGANISM: Homo sapiens
<220> FEATURE:
<223> OTHER INFORMATION: Amino acid sequence of IRF-2 protein

<400> SEQUENCE: 7

```
Met Pro Val Glu Arg Met Arg Met Arg Pro Trp Leu Glu Glu Gln Ile
  1               5                  10                  15

Asn Ser Asn Thr Ile Pro Gly Leu Lys Trp Leu Asn Lys Glu Lys Lys
             20                  25                  30

Ile Phe Gln Ile Pro Trp Met His Ala Ala Arg His Gly Trp Asp Val
         35                  40                  45

Glu Lys Asp Ala Pro Leu Phe Arg Asn Arg Ala Ile His Thr Gly Lys
     50                  55                  60

His Gln Pro Gly Val Asp Lys Pro Asp Pro Lys Thr Trp Lys Ala Asn
 65                  70                  75                  80

Phe Arg Cys Ala Met Asn Ser Leu Pro Asp Ile Glu Glu Val Lys Asp
                 85                  90                  95

Lys Ser Ile Lys Lys Gly Asn Asn Ala Phe Arg Val Tyr Arg Met Leu
            100                 105                 110

Pro Leu Ser Glu Arg Pro Ser Lys Lys Gly Lys Lys Pro Lys Thr Glu
        115                 120                 125

Lys Glu Asp Lys Val Lys His Ile Lys Gln Glu Pro Val Glu Ser Ser
    130                 135                 140

Leu Gly Leu Ser Asn Gly Val Ser Asp Leu Ser Pro Glu Tyr Ala Val
145                 150                 155                 160

Leu Thr Ser Thr Ile Lys Asn Glu Val Asp Ser Thr Val Asn Ile Ile
                165                 170                 175

Val Val Gly Gln Ser His Leu Asp Ser Asn Ile Glu Asn Gln Glu Ile
            180                 185                 190

Val Thr Asn Pro Pro Asp Ile Cys Gln Val Val Glu Val Thr Thr Glu
        195                 200                 205

Ser Asp Glu Gln Pro Val Ser Met Ser Glu Leu Tyr Pro Leu Gln Ile
    210                 215                 220

Ser Pro Val Ser Ser Tyr Ala Glu Ser Glu Thr Thr Asp Ser Val Pro
225                 230                 235                 240

Ser Asp Glu Glu Ser Ala Glu Gly Arg Pro His Trp Arg Lys Arg Asn
                245                 250                 255

Ile Glu Gly Lys Gln Tyr Leu Ser Asn Met Gly Thr Arg Gly Ser Tyr
            260                 265                 270

Leu Leu Pro Gly Met Ala Ser Phe Val Thr Ser Asn Lys Pro Asp Leu
        275                 280                 285

Gln Val Thr Ile Lys Glu Glu Ser Asn Pro Val Pro Tyr Asn Ser Ser
    290                 295                 300

Trp Pro Pro Phe Gln Asp Leu Pro Leu Ser Ser Ser Met Thr Pro Ala
305                 310                 315                 320

Ser Ser Ser Ser Arg Pro Asp Arg Glu Thr Arg Ala Ser Val Ile Lys
                325                 330                 335

Lys Thr Ser Asp Ile Thr Gln Ala Arg Val Lys Ser Cys
            340                 345
```

<210> SEQ ID NO 8
<211> LENGTH: 9
<212> TYPE: DNA
<213> ORGANISM: Artificial Sequence
<220> FEATURE:
<223> OTHER INFORMATION: IFN-gamma activaled sille (GAS) Consensus
      Sequence
<220> FEATURE:
<221> NAME/KEY: misc_feature
<222> LOCATION: 3
<223> OTHER INFORMATION: n = a, c, g, or t
<220> FEATURE:
<221> NAME/KEY: misc_feature
<222> LOCATION: (5)..(7)
<223> OTHER INFORMATION: n = a, c, g, or t

<400> SEQUENCE: 8 ttncnnnaa                                                                9

<210> SEQ ID NO 9
<211> LENGTH: 13
<212> TYPE: DNA
<213> ORGANISM: Artificial Sequence
<220> FEATURE:
<223> OTHER INFORMATION: IFN-alpha stimulated response element (ISRE)
      consensus Sequence
<220> FEATURE:
<221> NAME/KEY: misc_feature
<222> LOCATION: 1
<223> OTHER INFORMATION: n = a, c, g, or t
<220> FEATURE:
<221> NAME/KEY: misc_feature
<222> LOCATION: (6)..(7)
<223> OTHER INFORMATION: n = a, c, g, or t

<400> SEQUENCE: 9
ngaaanngaa act                                                          13

<210> SEQ ID NO 10
<211> LENGTH: 9
<212> TYPE: DNA
<213> ORGANISM: Artificial Sequence
<220> FEATURE:
<221> NAME/KEY:
<222> LOCATION:
<223> OTHER INFORMATION: Primer ISRE2

<400> SEQUENCE: 10 ttcccagaa                                                                9

<210> SEQ ID NO 11
<211> LENGTH: 13
<212> TYPE: DNA
<213> ORGANISM: Artificial Sequence
<220> FEATURE:
<221> NAME/KEY:
<222> LOCATION:
<223> OTHER INFORMATION: Primer ISRE2

<400> SEQUENCE: 11
ggaaactgaa act                                                          13

<210> SEQ ID NO 12
<211> LENGTH: 29
<212> TYPE: DNA
<213> ORGANISM: Artificial Sequence
<220> FEATURE:
<223> OTHER INFORMATION: ISRE-F2 probe

<400> SEQUENCE: 12
aatttctggg aaactgaaac tgaaaacct                                                29

<210> SEQ ID NO 13
<211> LENGTH: 29
<212> TYPE: DNA
<213> ORGANISM: Artificial Sequence
<220> FEATURE:
<223> OTHER INFORMATION: ISRE-F2 probe

<400> SEQUENCE: 13
aattaggttt tcagtttcag tttcccaga                                                29

<210> SEQ ID NO 14
<211> LENGTH: 36
<212> TYPE: DNA
<213> ORGANISM: Artificial Sequence
<220> FEATURE:
<223> OTHER INFORMATION: adp-1 probe

<400> SEQUENCE: 14
catggcatct acttcgtatg actattgcag agtgcc                                        36

<210> SEQ ID NO 15
<211> LENGTH: 36
<212> TYPE: DNA
<213> ORGANISM: Artificial Sequence
<220> FEATURE:
<223> OTHER INFORMATION: adp-2 probe

<400> SEQUENCE: 15
catgggcact ctgcaatagt catacgaagt agatgc                                        36

<210> SEQ ID NO 16
<211> LENGTH: 29
<212> TYPE: DNA
<213> ORGANISM: Artificial Sequence
<220> FEATURE:
<223> OTHER INFORMATION: Primer HM2k

<400> SEQUENCE: 16
aaaggtacca gctgtctttc tgtctgtcc                                                29

<210> SEQ ID NO 17
<211> LENGTH: 28
<212> TYPE: DNA
<213> ORGANISM: Artificial Sequence
<220> FEATURE:
<223> OTHER INFORMATION: Primer BST2B

<400> SEQUENCE: 17
atagtcatac gaagtagatg ccatccag                                                 28

<210> SEQ ID NO 18
<211> LENGTH: 28
<212> TYPE: DNA
<213> ORGANISM: Artificial Sequence
<220> FEATURE:
<223> OTHER INFORMATION: Primer 10S

<400> SEQUENCE: 18
tttcggtacc taattaatcc tctgcctg                                                 28

<210> SEQ ID NO 19
<211> LENGTH: 23
<212> TYPE: DNA
<213> ORGANISM: Artificial Sequence

```
<220> FEATURE:
<223> OTHER INFORMATION: GL Primer 2

<400> SEQUENCE: 19
ctttatgttt ttggcgtctt cca                                              23

<210> SEQ ID NO 20
<211> LENGTH: 30
<212> TYPE: DNA
<213> ORGANISM: Artificial Sequence
<220> FEATURE:
<223> OTHER INFORMATION: Primer HMP700

<400> SEQUENCE: 20
aaaggtacca gagtttacct ggtatcctgg                                       30

<210> SEQ ID NO 21
<211> LENGTH: 39
<212> TYPE: DNA
<213> ORGANISM: Artificial Sequence
<220> FEATURE:
<223> OTHER INFORMATION: Primer 11A'

<400> SEQUENCE: 21
cagaggatta attaggtacc gaaagagagg tgggctttt                             39

<210> SEQ ID NO 22
<211> LENGTH: 24
<212> TYPE: DNA
<213> ORGANISM: Artificial Sequence
<220> FEATURE:
<223> OTHER INFORMATION: Primer IRF2-F2

<400> SEQUENCE: 22
ttgtattggt agcgtgaaaa aagc                                             24

<210> SEQ ID NO 23
<211> LENGTH: 24
<212> TYPE: DNA
<213> ORGANISM: Artificial Sequence
<220> FEATURE:
<223> OTHER INFORMATION: Primer IRF2-R2

<400> SEQUENCE: 23
cagctagttc acattatctc gtcc                                             24

<210> SEQ ID NO 24
<211> LENGTH: 30
<212> TYPE: DNA
<213> ORGANISM: Artificial Sequence
<220> FEATURE:
<223> OTHER INFORMATION: Primer IRF2-F1

<400> SEQUENCE: 24
agagggtacc atgccggtgg aaaggatgcg                                       30

<210> SEQ ID NO 25
<211> LENGTH: 30
<212> TYPE: DNA
<213> ORGANISM: Artificial Sequence
<220> FEATURE:
<223> OTHER INFORMATION: Primer IRF2-R1

<400> SEQUENCE: 25
agtcggtacc ttaactgctc ttgacgcggg                                       30
```

THERAPEUTIC AGENT FOR HEMATOPOIETIC TUMORS

FIELD OF THE INVENTION

The present invention relates to the use of interferon α, interferon γ, and the IRF-2 protein as expression-enhancing agents for HM1.24 antigen in myeloma.

The present invention also relates to the use of interferon α, interferon γ, and the IRF-2 protein as expression-enhancing agents for HM1.24 antigen in lymphatic tumors. Furthermore, the present invention relates to a method of treating leukemia using anti-HM1.24 antibody and interferon α or interferon γ.

BACKGROUND ART

Leukocytes occurring in normal human peripheral blood comprise granulocytes, monocytes and lymphocytes, and granulocytes are further divided into neutrophils, eosinophils, and basophils. In the production of these blood cells, myelocytic stem cells and lymphatic stem cells differentiate from common undifferentiated hematopoietic stem cells, and from these stem cells, finally, each line of leukocytes differentiates. Blood cell-related cells including these hematopoietic stem cells are also referred to as hematopoietic cells. Tumors (hematopoietic tumors) of hematopoietic cells include leukemia, lymphoma, myeloma, and the like.

Leukemia is a disease of cancerated hematopoietic cells, in which bone marrow is occupied by leukemic cells and thereby normal hematopoietic functions are inhibited, resulting in the decreased production of normal blood cells and in subsequent development of anemia, leukopenia and thrombocytopenia. Also, based on the origin of leukemic cells, leukemia is roughly divided into two types: myelocytic leukemia and lymphocytic leukemia, each of which is further divided into the acute form and the chronic form. Furthermore, as a subtype, mixed lineage leukemia having cellular traits of the two lineages, bone marrow lineage and lymphocyte lineage, is also known.

Tumorigenesis takes place at the level of hematopoietic stem cells, wherein there are a case in which differentiation stops at a certain stage of differentiation and maturation and tumors are only formed in the cells upstream thereof, and a case in which the functions of differentiation and maturation are retained though it evades the biological regulatory functions and exhibits autonomous growth. The former includes acute leukemia, and the latter includes chronic leukemia and the myelodysplastic syndrome. Based on the identity of the growing cells, acute leukemia is roughly divided into acute myelocytic leukemia (AML), acute monocytic leukemia (AMoL), acute erythroleukemia, megakaryobalastic leukemia, and acute lymphocytic leukemia (ALL).

As a subtype, acute promyelocytic leukemia (APL) is known. Acute leukemia and the myelodysplastic syndrome may be classified based on the French-American-British classification (FAB classification). In the FAB classification, acute lymphocytic leukemia is divided into L1, L2, and L3, and for example Burkitt's lymphoma is classified into L3. Acute myelocytic leukemia is divided into M0, M1, M2, M3, M4, M5, M6, and M7 and, for example, erythrocyte abnormality is classified into M6 and megakaryobalastic leukemia is classified into M7. These methods of classification and of testing are known and are described in many textbooks (for example, Shin-Rinsho Naikagaku (New Clinical Internal Medicine), Fumimaro Takaku and Etsuro Ogata, Igakushoin Ltd., 1999).

Also, based on the identity of growing cells, chronic leukemia is roughly divided into chronic myelocytic leukemia (CML) and chronic lymphocytic leukemia (CLL). Also, as a subtype of chronic myelocytic leukemia, chronic myelomonocytic leukemia is known, and as a subtype of chronic lymphocytic leukemia, prolymphocytic leukemia is known.

Lymphoma is a generic term for tumors derived from cells constituting lymphatic tissues such as the lymph node, and is hematopoietic cell tumors caused mainly by canceration of lymphocytes. Malignant lymphoma is divided into Hodgkin's disease and non-Hodgkin lymphoma, both of which are cancerated lymphocytic cells and can be divided into the T lymphocytic and the B lymphocytic types.

As non-Hodgkin lymphoma, there are known B lymphocytic tumors such as follicular lymphoma, mantle cell lymphoma, Burkitt's lymphoma, pre-B lymphoma and the like. For T lymphocytic tumors, there are known adult T cell leukemia (ATL) and peripheral non-ATL T-lymphoma (PNTL). Also, diffuse lymphoma comprising two types (T lymphocytic and B lymphocytic) is included in non-Hodgkin lymphoma. Furthermore, as a subtype, hairy cell leukemia which is a B lymphocytic tumor is known.

Lymphocytic leukemia and lymphoma which are canceration of major constituent cells of lymphocytes are referred to as lymphocytic tumors, and are roughly divided into B lymphocytic tumors and T lymphocytic tumors. For example, B lymphocytic tumors include acute B lymphocytic leukemia (B-ALL), chronic B lymphocytic leukemia (B-CLL), pre-B lymphoma, Burkitt's lymphoma, follicular lymphoma, mantle cell lymphoma, diffuse lymphoma and the like. T lymphocytic tumors include acute T lymphocytic leukemia (T-ALL), chronic T lymphocytic leukemia (T-CLL), adult T cell leukemia (ATL), peripheral non-ATL T-lymphoma (PNTL) and the like (Zukai Rinshogan series (Illustrated Clinical Cancer Series) No. 17, Leukemia and lymphoma, Takashi Sugimura et al., MEDICAL VIEW Co., Ltd., 1987; B Lymphocytic Tumors, Kiyoshi Takatsuki, Nishimura Co., Ltd., 1991; Shin-Rinsho Naikagaku (New Clinical Internal Medicine), Fumimaro Takaku and Etsuro Ogata, Igakushoin Ltd., 1999). Myeloma is also a type of lymphatic tumor, and exhibits characteristic clinical findings.

Myeloma which is also referred to as plasmacytoma and multiple myeloma is a neoplastic disease characterized by the accumulation of monoclonal plasma cells in the bone marrow. Myeloma is a disease in which plasma cells, i.e. terminally differentiated B cells that produce and secrete immunoglobulins, are monoclonally increased mainly in the bone marrow, and thus in the serum of patients with this disease, monoclonal immunoglobulins or components thereof, L chain, H chain, etc., can be detected.

For the treatment of myeloma, chemotherapeutic agents etc. have been used so far, but no effective therapeutic agents have been found that lead to the complete remission and the extension of the survival of patients. Thus, there has been a long-awaited need for agents having therapeutic effects based on a new mechanism of action. For lymphoma and leukemia as well, though moderately effective chemotherapy has been developed, new agents have been waited for due to adverse reactions.

On the other hand, Goto, T. et al. have reported a monoclonal antibody (mouse anti-HM1.24 antibody) that was obtained by immunizing mice with human plasma cells (Blood (1994) 84, 1922-1930). When anti-HM1.24 antibody was administered to a mouse transplanted with human myeloma cells, the antibody accumulated in tumor tissues in a specific manner (Masaaki Kosaka et al., Nippon Rinsho (Japan Clinical) (1995) 53, 627-635), suggesting that anti-HM1.24 antibody could be applied in the diagnosis of tumor localization by radioisotopic labeling, missile therapies such as radiotherapy, and the like.

In the above Blood (1994) 84, 1922-1930, it has been described that anti-HM1.24 antibody has an in vitro cytotoxicity on a human myeloma cell line RPMI8226. It has also been shown that chimeric anti-HM1.24 antibody, or anti-HM1.24 antibody that is mouse anti-HM1.24 antibody rendered chimeric, and a humanized reshaped anti-HM1.24 antibody, specifically bind to myeloma cells and have cytotoxicity (Blood (1999) 93, 3922-3920).

On the other hand, it has also been demonstrated for lymphocytic tumors that an antigen protein recognized by anti-HM1.24 antibody is expressed in lymphocytic tumors, and that anti-HM1.24 antibody has a cytotoxicity on lymphocytic tumors due to a CDC activity and an ADCC activity, and thereby exhibits anti-tumor effect (WO 98/35698). Thus, HM1.24 antigen has been highly expressed not only in myeloma cells that are terminally differentiated B cells but also in lymphocytic tumors, and anti-HM1.24 antibody that recognizes HM1.24 antigen is useful as a therapeutic agent for lymphocytic tumors.

Thus, HM1.24 antigen has been highly expressed in myeloma cells that are terminally differentiated B cells and in lymphocytic tumors, and anti-HM1.24 antibody that recognizes this antigen exhibits cell-killing activity in proportion to the number of HM1.24 antigens on the cell surface, and thus immunotherapy with anti-HM1.24 antibody is expected to provide an effective method of treating multiple myeloma and lymphocytic tumors. Thus, if the amount of HM1.24 antigen, which is an antigen against anti-HM1.24 antibody, expressed on the cell surface could be enhanced, the administration of a smaller amount of the antibody is expected to provide equivalent cytotoxicity, and it would become possible to decrease adverse reactions.

Furthermore, for hematopoietic tumor cells that are not expressing HM1.24 antigen, if the amount of HM1.24 antigen expressed on the cell surface could be enhanced, cytotoxicity or cytocidal effect through ADCC activity or CDC activity with anti-HM1.24 antibody is expected for hematopoietic tumor cells for which, generally, anti-HM1.24 antibody alone is not effective.

On the other hand, interferon, that was discovered as a substance having an activity of inhibiting viral growth, is currently known to be classified into four groups of α, β, γ, and ω̄ in mammals, and to have a variety of biological activities (Pestka, S., et al., Ann. Rev. Biochem. (1987) 56, 727-777; Langer, J. A., et al., Immunology Today (1988) 9, 393-400). However, there were no reports on whether interferon α and interferon γ could have an effect of increasing the expressed amount of HM1.24 antigen in myeloma cells or cells of hematopoietic tumors such as lymphocytic tumors.

On the other hand, interferon regulatory factor (IRF)-1 and 2 were identified as a transcription regulatory factor of the IFN-β gene. IRF-1 and 2 are generally known to bind to the same gene regulatory sequence, and act in an antagonistic manner in that IRF-1 acs as a transcription activation factor and IRF-2 as a transcription suppressing factor. The NIH3T3 cells in which IRF-2 was highly expressed has been demonstrated to exhibit enhanced cell saturation density, colony formation in the methylcellulose gel, and a tumorigenic property in nude mice, and IRF-2 has been shown to act as an oncogene.

On the other hand, recent advances in research have indicated that IRF-2 is required for the expression of histone H4 that acts in the control of cell cycle. IRF-2 has also been shown to increase the expression of vascular cell adhesion molecule-1 (VCAM-1) in muscle cells, and it has also been demonstrated that the acid region (182 to 218) of IRF-2 is involved in the activation of VCAM-1. Based on this, it is known that IRF-2 not only acts as a transcription regulatory factor but may act as a transcription activation factor.

However, it was not known that the IRF-2 protein binds to the promoter (HM1.24 promoter) of the HM1.24 antigen gene, and activates said promoter.

DISCLOSURE OF THE INVENTION

Current methods of treating myeloma are, as mentioned above, not satisfactory and, accordingly, the appearance of epoch-making therapeutic drugs or methods that prolong the patient's survival is awaited. The treatment of myeloma with anti-HM1.24 antibody is likely to provide epoch-making therapeutic drugs in terms of specificity and effectiveness, and thus there is a need for methods of allowing anti-HM1.24 antibody to exhibit its effect more efficiently.

Also, as methods of treating lymphocytic tumors currently employed, there can be mentioned various chemotherapies, X-ray therapy, bone marrow transplantation and the like, but no therapeutic methods are satisfactory, and thus epoch-making therapeutic drugs or methods that attains complete remission of lymphocytic tumors and prolong the patient's survival are awaited. Furthermore, therapeutic methods that are effective for leukemia other than lymphocytic leukemia, i.e. myelocytic leukemia such as acute myelocytic leukemia and chronic lymphocytic leukemia are awaited. Therapeutic drugs and methods that attain complete remission of these myelomas, lymphocytic tumors, and myelocytic leukemia and that can prolong the patient's survival could provide therapeutic drugs and methods for hematopoietic tumors in general.

Thus, it is an object of the present invention to provide a means of enhancing the effect of anti-HM1.24 antibody of suppressing myeloma by enhancing the amount expressed of HM1.24 antigen in myeloma.

It is another object of the present invention to provide a means of enhancing the effect of anti-HM1.24 antibody of suppressing lymphocytic tumors by enhancing the amount expressed of HM1.24 antigen in lymphocytic tumors.

It is further object of the present invention to provide a means of inducing the effect of anti-HM1.24 antibody of suppressing myelocytic leukemia by providing a means of newly inducing the expression of HM1.24 antigen in myelocytic leukemia.

The above should provide a means of treating hematopoietic tumors with anti-HM1.24 antibody by enhancing the amount expressed of HM1.24 antigen or by using a means of newly inducing HM1.24 antigen.

After searching drugs that either enhance the amount expressed of HM1.24 antigen or allow. HM1.24 antigen to be newly expressed on the cell surface, the present inventors have found that interferon α, interferon γ, and the IRF-2 protein have the desired activity, and thereby have completed the present invention.

Thus the present invention provides an expression-enhancing or expression-inducing agent of a protein (HM1.24 antigen) having the amino acid sequence set forth in SEQ ID NO: 2 in hematopoietic tumor cells, said agent comprising interferon α, interferon γ, or the IRF-2 protein as an active ingredient.

The above hematopoietic tumors are, for example, leukemia, lymphoma, myeloma etc., and as this leukemia includes, for example, acute myelocytic leukemia, chronic myelocytic leukemia, acute lymphocytic leukemia, chronic lymphocytic leukemia etc., the above lymphoma includes, for example, Hodgkin's disease, T lymphocytic non-Hodgkin lymphoma, B lymphocytic non-Hodgkin lymphoma etc., and the above myeloma includes multiple myeloma.

The present inventors have also found that, by allowing an antigen that specifically binds to said HM1.24 antigen to bind to the hematopoietic tumor cells in which HM1.24 antigen has been expressed by the above expression-enhancing or expression-inducing agent of HM1.24 antigen, anti-tumor effect on said hematopoietic tumor cells can be enhanced.

Thus, the present invention also provides a therapeutic agent or a pharmaceutical composition for the treatment of hematopoietic tumors comprising, as an active ingredient, an antibody that specifically binds to a protein having the amino acid sequence set forth in SEQ ID NO: 2, wherein interferon α, interferon γ, or the IRF-2 protein is used in combination.

The present invention also provides a therapeutic agent or a pharmaceutical composition for the treatment of hematopoietic tumors comprising, as an active ingredient, (1) interferon α, interferon γ, or the IRF-2 protein, and (2) an antibody that specifically binds to a protein having the amino acid sequence set forth in SEQ ID NO: 2.

The present invention also provides a therapeutic agent or a pharmaceutical composition for the treatment of hematopoietic tumors comprising, as an active ingredient, interferon α, interferon γ, or the IRF-2 protein, wherein an antibody that specifically binds to a protein having the amino acid sequence set forth in SEQ ID NO: 2 is used in combination.

The above hematopoietic tumors are, for example, leukemia, lymphoma, or myeloma. The above leukemia includes, for example, acute myelocytic leukemia, chronic myelocytic leukemia, acute lymphocytic leukemia, chronic lymphocytic leukemia etc., the above lymphoma includes, for example, Hodgkin's disease, T lymphocytic non-Hodgkin lymphoma, B lymphocytic non-Hodgkin lymphoma etc., and the above myeloma includes multiple myeloma.

The above antibody is preferably an antibody having cytotoxicity, and the cytotoxicity is the ADCC activity. The antibody is preferably a monoclonal antibody, a chimeric antibody, a humanized antibody, or a human antibody. The monoclonal antibody is preferably anti-HM1.24 antibody produced by a hybridoma having the Deposit No. FERM BP-5233, and said chimeric antibody or humanized antibody is preferably a chimeric antibody or a humanized antibody of anti-HM1.24 antibody produced by a hybridoma having the Deposit No. FERM BP-5233.

The present invention further provides a kit for the treatment of a patient having a hematopoietic tumor, said kit comprising:
(1) an antibody that specifically binds to a protein having the amino acid sequence set forth in SEQ ID NO: 2; and
(2) an instruction manual instructing the administration of the above antibody to the patient in combination with an expression-enhancing agent of a protein having the amino acid sequence set forth in SEQ ID NO: 2.

The present invention also provides a kit for the treatment of a patient having a hematopoietic tumor, said kit comprising:
(1) an expression-enhancing agent of a protein having the amino acid sequence set forth in SEQ ID NO: 2; and
(2) an instruction manual instructing the administration of the above antibody to the patient in combination with an antibody that specifically binds to a protein having the amino acid sequence set forth in SEQ ID NO: 2.

The present invention also provides a kit for the treatment of a patient having a hematopoietic tumor, said kit comprising:
(1) an expression-enhancing agent of a protein having the amino acid sequence set forth in SEQ ID NO: 2; and
(2) an antibody that specifically binds to a protein having the amino acid sequence set forth in SEQ ID NO: 2; and
(3) an instruction manual instructing the combined administration of the above agent and the above antibody to the patient.

The present invention also provides a method of screening an expression-enhancing agent of HM1.24 antigen, comprising the steps of:
(1) preparing cells having a reporter gene that has the region of the HM1.24 gene promoter;
(2) contacting said cells with a test substance; and
(3) detecting the expression of the reporter gene.

The present invention also provides an expression-enhancing agent of HM1.24 antigen selected by the above method.

The present invention also provides a pharmaceutical composition for the treatment of hematopoietic tumors wherein said composition comprises the above expression-enhancing agent and said composition is used in combination with an antibody that specifically binds to a protein having the amino acid sequence set forth in SEQ ID NO: 2.

The present invention further provides a method of screening an expression-enhancing agent comprising the steps of:
(1) contacting cells with a test substance;
(2) determining the amount expressed of the IL-2 protein in said cells.

The present invention also provides an expression-enhancing agent of the IRF-2 protein selected by the above method.

The present invention also provides a pharmaceutical composition for the treatment of hematopoietic tumors wherein said composition comprises the above expression-enhancing agent and said composition is used in combination with an antibody that specifically binds to a protein having the amino acid sequence set forth in SEQ ID NO: 2.

BRIEF EXPLANATION OF THE DRAWINGS

FIG. 1 shows the result of an experiment in which a myeloma cell line U266 cultured in the absence (upper) or the presence (bottom) of interferon α was analyzed by flow cytometry using human IgG (control) or anti-HM1.24 antibody as a label.

FIG. 2 shows the result of an experiment in which the myeloma cells of a patient cultured in the absence (upper) or the presence (bottom) of interferon α was analyzed by flow cytometry using human IgG (control) or anti-HM1.24 antibody as a label.

FIG. 5 shows the result of an experiment in which a myeloma cell line U266 cultured in the absence (upper) or the presence (bottom) of interferon γ was analyzed by flow cytometry using human IgG (control) or anti-HM1.24 antibody as a label.

FIG. 6 shows the result of an experiment in which the myeloma cells of the patient cultured in the absence (upper) or the presence (bottom) of interferon γ were analyzed by flow cytometry using human IgG (control) or anti-HM1.24 antibody as a label.

FIG. 12 shows the result of an experiment in which cells collected from a patient with T lymphocytic non-Hodgkin lymphoma were cultured in the absence (left) or the presence (right) of interferon α, and then were analyzed by flow cytometry using human IgG (control) or anti-HM1.24 antibody as a label. The dark area represents the control and the light area represents the stain with anti-HM1.24 antibody.

FIG. 13 shows the result of an experiment in which ADCC activity by various human anti-HM1.24 antibodies were determined when peripheral blood mononuclear cells from normal healthy subjects were used as the effector cell using a human leukemia cell line HEL as the standard cell.

EMBODIMENTS FOR CARRYING OUT THE INVENTION

Interferon-α and Interferon-γ

Figure 3:
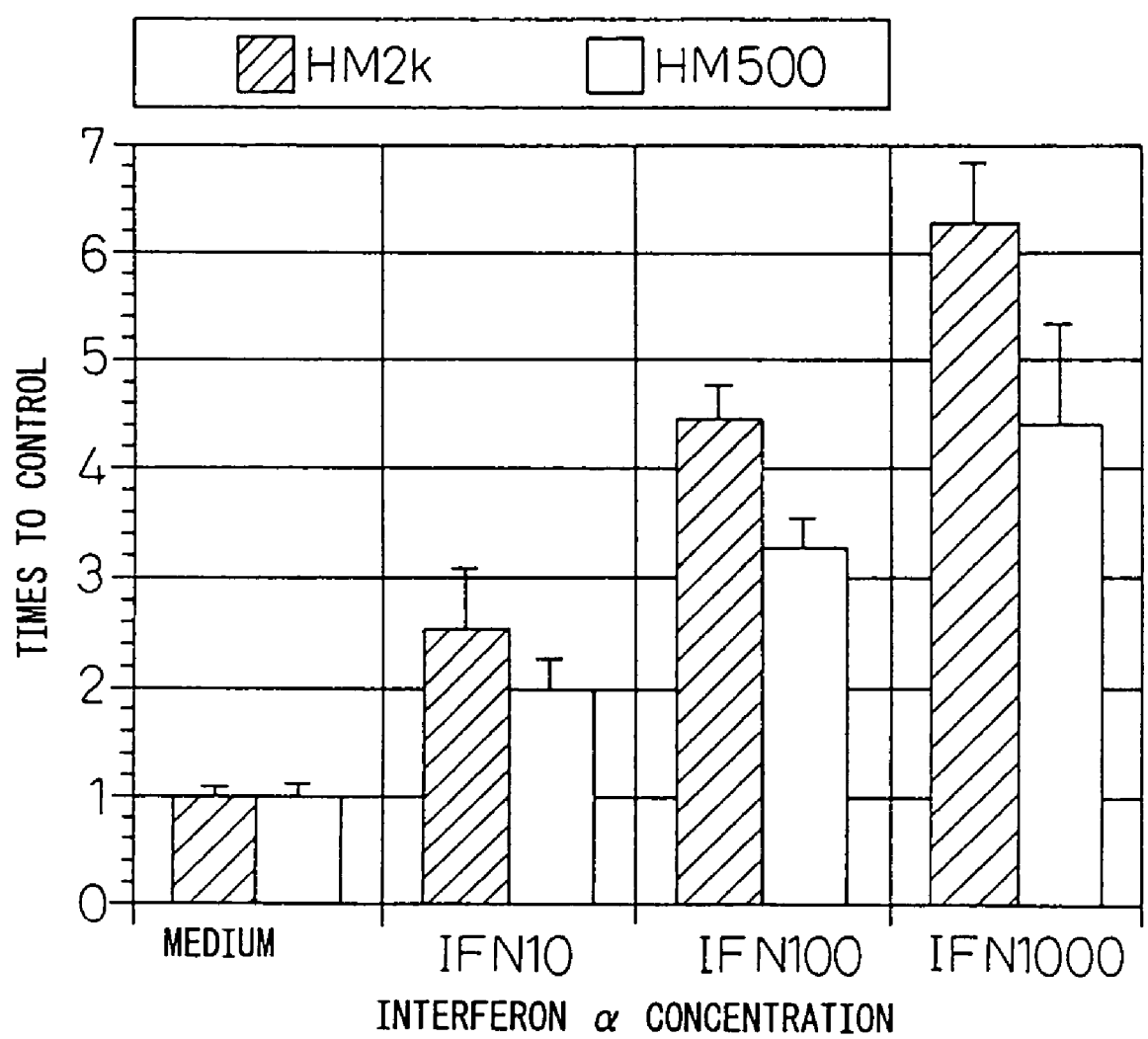
FIG. 3 is a graph showing the result of an experiment in which U266 cells transformed with a reporter plasmid into which the promoter region of a gene encoding HM1.24 antigen had been inserted were cultured in the absence or in the presence of various concentrations of interferon α, and then the luciferase activity was determined.

Interferon was discovered as a substance having an activity of inhibiting viral growth and currently four types, α, β, γ, and ω, are known in mammals. In addition to the activity of inhibiting viral growth, they are known to exhibit an activity of inhibiting cell growth and of modulating immunological functions (Interferon "Cytokine", Toshiaki Osawa etd., (1990) 115-133, Tokyo Kagaku Dojin Co., Ltd.; Pestka, S., et al., Ann. Rev. Biochem. (1987) 56, 727-777; Langer, J. A., et al., Immunology Today (1988) 9, 393-400).

Interferon-α and interferon-γ for use in the present invention may be mutants as long as they have an activity of increasing the amount expressed of HM1.24 antigen. In order to determine the amount expressed of HM1.24 antigen, as described in Examples, myeloma cells are harvested from a myeloma cell line or a patient with myeloma and then subjected to flow cytometry for detection. As mutants, they may be interferon-α and interferon-γ in which one or several, or a plurality of amino acid residues have been deleted, substituted, or substituted or inserted.

As methods of introducing deletion, substitution, or insertion into proteins, there can be used site-directed mutagenesis that alters the corresponding gene (Hashimoto-Gotoh, Gene (1005) 152, 271-275, Zoller, Methods Enzymol. (1983) 100, 468-500, Kramer, Nucleic Acids Res. (1984) 12, 9441-8456, Kunkel, Proc. Natl. Acad. Sci. USA (1985) 82, 489-492, "New Cell Engineering Experimental Protocol" edited by Dept. of Oncology, Inst. of Medical Science, Univ. of Tokyo (1993) pp. 241-248).

It is also possible to use "Site-Directed Mutagenesis System" (GIBCO-BRL) and "QuickChange Site-Directed Mutagenesis Kit" (Stratagene) employing commercially available PCR. Amino acid mutations in proteins may sometimes take place in nature. That such a protein, in which mutation has been introduced, has an activity equal to the original protein has been shown in Mark, Proc. Natl. Acad. Sci. USA (1984) 81, 5662-5666.

In the substitution of amino acid residues, it is preferred to substitute between amino acids whose properties are conserved. For example, substitution is preferred between hydrophobic amino acids (A, I, L, M, F, P, W, Y, V), hydrophilic amino acids (R, D, N, C, E, Q, G, H, K, S, T), amino acids having aliphatic side chains (G, A, V, L, I, P), amino acids having hydroxyl group-containing side chains (S, T, Y), amino acids having sulfur-containing side chains (C, M), amino acids having carboxylic acid- and amide-containing side chains (D, N, E, Q), amino acids having base-containing side chains (R, K, H), and amino acids having aromatic group-containing side chains (H, F, Y, W).

Furthermore, as mutants, peptide fragments of interferon-α or interferon-γ may be used. In particular, peptide fragments that have binding sites with interferon-α or interferon-γ receptors are preferred. Preferably they are peptides comprised of 100 or more, more preferably 130 or more, still more preferably 150, and most preferably 160 or more contiguous amino acid residues.

IRF-2 Protein

Interferon regulatory factors (IRF)-1 and -2 were identified as transcription regulatory factors of the IFN-β gene (Taniguchi, T. et al., Nucleic Acids Res. (1989) 17, 8372; Taniguchi, T. et al., Cell (1989) 58, 729). IRF-1 and -2 are generally known to bind to the same gene regulatory sequence: IRF-1 and IRF-2 act in an antagonistic manner in that IRF-1 acs as a transcription activation factor, whereas IRF-2 as a transcription suppressing factor. The NIH3T3 cells in which IRF-2 is highly expressed has been demonstrated to exhibit enhanced cell saturation density, colony formation in the methylcellulose gel, and a tumorigenic property in nude mice, and IRF-2 acts as an oncogene.

On the other hand, recent advances in research have indicated that IRF-2 is required for the expression of histone H4 that acts for the control of cell cycle. IRF-2 is also shown to increase the expression of vascular cell adhesion molecule-1 (VCAM-1) in muscle cells, and it is becoming increasingly clear that the acid region (182 to 218) of IRF-2 is involved in the activation of VCAM-1. Based on this, it is known that IRF-2 not only acts as a transcription regulatory factor but as a transcription activation factor.

Hybridoma

The hybridoma that produces the antibody for use in the present invention can be basically constructed using a known technology as described below. Thus, the HM1.24 antigen protein or a HM1.24 antigen-expressing cell may be used as a sensitizing antigen and is immunized in the conventional method of immunization. The immune cells thus obtained are fused with known parent cells in the conventional cell fusion process, and then monoclonal antibody-producing cells are screened by the conventional screening method to construct the desired hybridoma.

Specifically, monoclonal antibody may be obtained in the following manner. For example, as the HM1.24 antigen-expressing cell which is the sensitizing antigen to obtain antibody, a human multiple myeloma cell line KPMM2 (Japanese Unexamined Patent Publication (Kokai) No. 7-236475) and KPC-32 (Goto, T. et al., Jpn. J. Clin. Hematol. (1991) 32, 1400) can be used. As the sensitizing antigen, it is also possible to use a protein having the amino acid sequence set forth in SEQ ID NO: 1 or a peptide or a polypeptide containing an epitope recognized by anti-HM1.24 antibody.

The CDNA of the protein having the amino acid sequence set forth in SEQ ID NO 1 used as the sensitizing antigen may be inserted into the XbaI cleavage site of the pUC19 vector to prepare a plasmid pRS38-pUC19. *E. coli* having the plasmid pRS38-pUC19 has been internationally deposited under the provisions of the Budapest Treaty as *Escherichia coli* DH5α (pRS38-pUC19) on Oct. 5, 1993 with the Patent Microorganism Depository, the National Institute of Bioscience and Human Technology (Chuo Dai 6, 1-1, Higashi 1-chome, Tsukuba city, Ibaraki Pref., Japan) as FERM BP-4434 (Japanese Unexamined Patent Publication (Kokai) No. 7-196694). Using the cDNA fragment contained in this plasmid pRS38-pUC19, a peptide or a polypeptide that contains an epitope recognized by anti-HM1.24 antibody can be constructed by gene engineering technology.

Mammals to be immunized with the sensitizing antigen are not specifically limited, and they are preferably selected in consideration of their compatibility with the parent cell for use in cell fusion. They generally include rodents such as mice, rats, and hamsters.

Immunization of animals with a sensitizing antigen may be carried out using a known method. A general method, for example, involves the intraperitoneal or subcutaneous administration of a sensitizing antigen to the mammal.

Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to the mammal for several times every 4 to 21 days. Alternatively, a suitable carrier may be used at the time of immunization of the sensitizing antigen.

After immunizing in this manner and confirming an increase in the desired antibody levels in the serum, immune cells are harvested from the mammal and are subjected to cell fusion. As immune cells to be subjected to cell fusion, there may be specifically mentioned spleen cells.

The mammalian myeloma cells as the other parent cells which are subjected to cell fusion with the above-mentioned immune cells preferably include various known cell lines such as P3X63Ag8.653 (J. Immunol. (1979) 123: 1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al. J. Immunol. Methods (1980) 35: 1-21), S194 (Trowbridge, I. S., J. Exp. Med. (1978) 148: 313-323), R210 (Galfre, G. et al., Nature (1979) 277: 131-133) and the like.

Cell fusion between the above immune cells and the myeloma cells may be essentially conducted in accordance with a known method such as is described in Milstein et al. (Kohler, G. and Milstein, C., Methods Enzymol. (1981) 73: 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of the fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v), and mixed to obtain the desired fusion cells (hybridomas). Then by repeating the sequential addition of a suitable culture liquid and centrifugation to remove the supernatant, cell fusion agents etc. which are undesirable for the growth of the hybridoma can be removed.

Said hybridoma is selected by culturing in a conventional selection medium, for example, the HAT culture medium (a culture liquid containing hypoxanthine, aminopterin, and thymidine). Culturing in said HAT culture medium is continued generally for a period of time sufficient to effect killing of the cells (non-fusion cells) other than the desired hybridoma, generally several days to several weeks. Then, the conventional limiting dilution method is conducted in which the hybridomas that produce the desired antibody are screened and monoclonally cloned.

In addition to obtaining the above hybridoma by immunizing an animal other than the human with an antigen, it is also possible to sensitize human lymphocytes in vitro with HM1.24 antigen or HM1.24 antigen-expressing cells, and to allow the resulting sensitized lymphocytes to be fused with a human myeloma cell, for example U266, and thereby to obtain the desired human antibody having the activity of binding to HM1.24 antigen or to HM1.24 antigen-expressing cells (see Japanese Examined Patent Publication (Kokoku) No. 1-59878). Furthermore, a transgenic animal having a repertoire of human antibody genes is immunized with HM1.24 antigen or HM1.24 antigen-expressing cells to obtain the desired antibody according to the above-mentioned method (see International Patent Publication WO 93/12227, WO 92/03918, WO 94/02602, WO 94/25585, WO 96/34096, and WO 96/33735).

Furthermore, using a human antibody library, the desired human antibody may be isolated by means of panning. For example, the variable region of human antibody is expressed on the surface of a phage by the phage display method as a single chain antibody (scFv) to select a phage that binds to the HM1.24 antigen using a HM1.24 antigen-immobilized plate. By analyzing the gene of the phage selected, the gene encoding the variable region of the human antibody that binds to the HM1.24 antigen can be identified. Using these gene sequences, anti-HM1.24 antibody can be prepared. These methods are already known and can be found in WO 92/01047, WO 92/20791, WO 93/06213, WO 93/11236, WO 93/19172, WO 95/01438, and WO 95/15388.

The monoclonal antibody-producing hybridomas thus constructed can be subcultured in the conventional culture liquid, or can be stored for a prolonged period of time in liquid nitrogen.

In order to obtain monoclonal antibodies from said hybridoma, there may be employed a method in which said hybridoma is cultured by the conventional method and the antibodies are obtained as the culture supernatant, or a method in which the hybridoma is administered to and grown in a mammal compatible with said hybridoma and the antibodies are obtained as the ascites, or other methods. The former method is suitable for obtaining high-purity antibodies, whereas the latter is suitable for a large scale production of antibodies.

Monoclonal Antibody

Specifically the anti-HM1.24 antibody-producing hybridoma can be constructed using the method of Goto, T. et al. (Blood (1994) 84: 1922-1930). It can be conducted by: a method in which the anti-HM1.24 antibody-producing hybridoma that was internationally deposited under the provisions of the Budapest Treaty as FERM BP-5233 on Apr. 27, 1995 with the Patent Microorganism Depository, the National Institute of Bioscience and Human Technology (Chuo Dai 6, 1-1, Higashi 1-chome, Tsukuba city, Ibaraki Pref., Japan) is intraperitoneally injected to BALB/c mice (manufactured by CLEA Japan) to obtain the ascites, from which the anti-HM1.24 antibody is purified, or: a method in which said hybridoma is cultured in a suitable culture medium such as the RPMI1640 medium containing 10% bovine fetal serum and 5% BM-Condimed H1 (manufactured by Boehringer Mannheim), the hybridoma SFM medium (manufactured by GIBCO-BRL), the PFHM-II medium (manufactured by GIBCO-BRL) and the like, and the anti-HM1.24 antibody can be purified from the supernatant.

Recombinant Antibody

A recombinant antibody which was produced by the recombinant gene technology, in which an antibody gene was cloned from the hybridoma and integrated into a suitable vector which was then introduced into a host, can be used in the present invention as monoclonal antibody (see, for example, Carl, A. K., Borrebaeck, and James, W. Larrick, THERAPEUTIC MONOCLONAL ANTIBODIES, published in the United Kingdom by MACMILLAN PUBLISHERS LTD. 1990).

Specifically, mRNA encoding the variable region (V) of the desired antibody is isolated from the hybridoma producing the antibody. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chmczynski, P. et al., (1987) 162, 156-159), and then mRNA is purified from the total RNA using the mRNA Purification kit (manufactured by Pharmacia) and the like. Alternatively, mRNA can be directly prepared using the QuickPrep mRNA Purification Kit (manufactured by Pharmacia).

cDNA of the V region of the antibody may be synthesized using a reverse transcriptase from the mRNA thus obtained. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932) that employs PCR may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of the expression regulatory region, for example an enhancer and/or a promoter. Subsequently, the expression vector may be transformed into a host cell and the antibody can then be expressed therein.

Altered Antibody

In accordance with the present invention, artificially altered recombinant antibody such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Publication WO 96/02576). Using this known method, chimeric antibody useful for the present invention can be obtained.

For example, E. coli having the plasmid that contains the L chain and the H chain of chimeric anti-HM1.24 antibody has been internationally deposited under the provisions of the Budapest Treaty as *Escherichia coli* DH5α (pUC19-1.24L-gκ) and *Escherichia coli* DH5α (pUC19-1.24H-gγ1), respectively, on Aug. 29, 1996 with the Patent Microorganism Depository, the National Institute of Bioscience and Human Technology (Chuo Dai 6, 1-1, Higashi 1-chome, Tsukuba city, Ibaraki Pref., Japan) as FERM BP-5646 and FERM BP-5644, respectively (see Japanese Patent Application No. 8-264756).

Humanized antibody which is also referred to as reshaped human antibody has been made by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Publication WO 96/02576).

Specifically, a DNA sequence which was designed to ligate the CDR of mouse antibody with the framework region (FR) of human antibody is synthesized by the PCR method from several divided oligonucleotides having sections overlapping with one another at the ends thereof. The DNA thus obtained is ligated to the DNA encoding the C region of human antibody, and then is integrated into an expression vector, which is introduced into a host for antibody production (see European Patent Application EP 239400 and International Patent Publication WO 96/02576).

For the FR of human antibody ligated through CDR, the FR is selected for which the complementarity determining region forms a favorable antigen binding site. When desired, amino acids in the framework region of the antibody variable region may be substituted so that the complementarity determining region of reshaped human antibody may form an appropriate antigen binding site (Sato, K. et al., Cancer Res. (1993) 53, 851-856).

For example, E. coli having the plasmid that contains the L chain and the H chain of humanized anti-HM1.24 antibody has been internationally deposited under the provisions of the Budapest Treaty as *Escherichia coli* DH5α (pUC19-RVLa-AHM-gκ) and *Escherichia coli* DH5α (pUC19-RVHr-AHM-gγ1), respectively, on Aug. 29, 1996 with the Patent Microorganism Depository, the National Institute of Bioscience and Human Technology (Chuo Dai 6, 1-1, Higashi 1-chome, Tsukuba city, Ibaraki Pref., Japan) as FERM BP-5645 and FERM BP-5643, respectively (Patent Application No. 8-264756).

For chimeric antibody or humanized antibody, the C region of human antibody is used and, as the C region of human antibody that exhibits cytotoxicity, human Cγ, for example Cγ1, Cγ2, Cγ3, and Cγ4, can be used. Among them, antibody having Cγ1 and Cγ3 in particular has potent cytotoxicity, i.e. ADCC activity and CDC activity, and is used preferably in the present invention.

Chimeric antibody consists of the variable region of antibody derived from a mammal other than the human and the C region derived from human antibody, whereas humanized antibody consists of the complementarity determining region of antibody derived from a mammal other than the human and the framework region (FR) and the C region of antibody derived from human antibody. Accordingly, antigenicity thereof in the human body has been reduced so that they are useful as the active ingredient of the therapeutic agents of the present invention.

A preferred embodiment of the humanized antibody for use in the present invention includes humanized anti-HM1.24 antibody (see WO 98/14580).

Expression and Production

Antibody genes constructed as described above may be expressed and obtained in a known method. In the case of mammalian cells, expression may be accomplished using an expression vector containing a commonly used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for the expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Nature (1979) 277, 108) when SV40 promoter/enhancer is used, or by the method of Mizushima et al. (Nucleic Acids Res. (1990) 18, 5322) when HEF1α promoter/enhancer is used.

In the case of E. coli, expression may be conducted by operably linking a commonly used useful promoter, a signal sequence for antibody secretion, and the antibody gene to be expressed, followed by expression thereof. As the promoter, for example, there can be mentioned lacZ promoter and araB promoter. The method of Ward et al. (Nature (1098) 341, 544-546; FASEB J. (1992) 6, 2422-2427) may be used when lacz promoter is used, and the method of Better et al. (Science (1988) 240, 1041-1043) may be used when araB promoter is used.

As the signal sequence for antibody secretion, when produced in the periplasm of E. coli, the pelB signal sequence (Lei, S.P. et al., J. Bacteriol. (1987) 169, 4379) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside transferase (APH) gene, the thymidine kinase (TK) gene, E. coli xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro and the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as Xenopus oocytes, or (3) insect cells such as sf9, sf21, and Tn5. Known plant cells include, for example, those derived from the genus *Nicotiana*, more specifically cells derived from *Nicotiana tabacum*, which is subjected to callus culture. Known fungal cells include yeasts such as the genus *Saccharomyces*, more specifically *Saccharomyces cereviceae*, or filamentous fungi such as the genus *Aspergillus*, more specifically Aspergillus niger.

When the prokaryotic cells are used, there are the production systems which employ bacterial cells. Known bacterial cells include *Escherichia coli* (*E. coli*), and *Bacillus subtilis*.

By introducing, via transformation, the gene of the desired antibody into these cells and culturing the transformed cells in vitro, the antibody can be obtained. Culturing is conducted in the known methods. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As further in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). As insects, silkworms can be used.

When plants are used, tabacco, for example, can be used.

Antibody genes are introduced into these animals or plants, and the antibodies are produced in such animals or plants, and recovered therefrom. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat born to the goat who received the embryo or offsprings thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Susumu, M. et al., Nature (1985) 315, 592-594). Moreover, when tabacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tabacco (Julian, K.-C. Ma et al., Eur. J. Immunol. (1994) 24, 131-138).

When antibody is produced in the in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Publication WO 94-11523).

The antibody produced as described above can be bound to various molecules such as polyethylene glycol (PEG) for use as a modified antibody. "Antibody" as used herein includes these modified antibodies. In order to obtain these modified antibody, the antibody obtained may be chemically modified. These methods have already been established in the field of the art.

Separation and Purification of Antibody

Antibodies produced and expressed as described above can be separated from the inside or outside of the cell or from the host and then may be purified to homogeneity. Separation and purification of the antibody for use in the present invention may be accomplished by affinity chromatography. As the column used for such affinity chromatography, there can be mentioned Protein A column and Protein G column. Examples of the column employing Protein A column are Hyper D, POROS, Sepharose F. F. and the like.

Alternatively, methods for separation and purification conventionally used for proteins can be used without any limitation. Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like.

Determination of Antibody Concentration

The concentration of antibody obtained in the above method can be determined by the measurement of absorbance or by ELISA and the like. Thus, when absorbance measurement is employed, the antibody for use in the present invention or a sample containing the antibody is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 μl of goat anti-human IgG (manufactured by BIO SOURCE) diluted to 1 μg/ml in 0.1 M bicarbonate buffer, pH 9.6, is added to a 96-well plate (manufactured by Nunc), and is incubated overnight at 4° C. to immobilize the antibody.

After blocking, 100 ml each of appropriately diluted antibody of the present invention or a sample containing the antibody, or 100 ml of human IgG (manufactured by CAPPEL) as the standard is added, and incubated at room temperature for 1 hour. After washing, 100 l of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

FCM Analysis

Reactivity of the antibody of the present invention with lymphocytes may be examined by flow cytometry (FCM) analysis. As the cells, established cell lines or freshly isolated cells can be used. As established cell lines, there may be used myeloma-derived RPMI8226 (ATCC CCL 155), myeloma-derived U266 (ATCC TIB 196), myeloma-derived KPMM2, myeloma-derived KPC-32, and plasmacytoma-derived ARH-77 (ATCC CRL 1621), and the like.

After washing the above cells in PBS(−), 100 μl of antibody or a control antibody diluted to 25 μg/ml in the FACS buffer (PBS(−) containing 2% bovine fetal serum and 0.05% sodium azide) is added thereto, which is then incubated on ice for 30 minutes. After washing with the FACS buffer, 100 μl of 25 μg/ml FITC-labeled goat anti-mouse antibody (GAM, manufactured by Becton Dickinson) is added thereto, which is then incubated on ice for 30 minutes. After washing with the FACS buffer, the cells are suspended in 600 μl of 1 ml of the FACS buffer, and each cell may be measured for its fluorescence intensity using the FACScan (manufactured by Becton Dickinson).

Screening Method

In order to screen the expression enhancer of HM1.24 antigen, for example, the cells that have not been stimulated and that are not expressing HM1.24 antigen or the cells that at least are expressing the antigen are determined using FCM analysis. For example, the cells described in Examples and a test substance are incubated for 1-2 days, and then stained with mouse anti-human HM1.24 antibody as a primary antibody. The cells are washed and further stained with FITC-labeled anti-mouse IgG antibody as a secondary antibody. Finally, after washing the cells, the fluorescence intensity of FITC is measured by a flow cytometer.

Furthermore, instead of the above indirect staining, FCM analysis by direct staining may be used in which the cells are treated with a high concentration of immunoglobulin, and then stained, after blocking Fc receptors, with FITC-labeled anti-human HM1.24 antibody.

It is also possible to screen expression enhancers of HM1.24 antigen by the reporter gene assay using the HM1.24 promoter sequence. As the reporter gene, luciferase can be used. A plasmid is constructed that contains the HM1.24 promoter sequence upstream of the reporter gene, after which it is transformed into the cells, and the cells obtained are cultured with a test substance for 1-2 days, and the cells recovered are subjected to FCM analysis to screen drugs that enhance the expression of HM1.24 antigen.

Cytotoxicity
Measurement of ADCC Activity

The antibody for use in the present invention is one which has, for example, an ADCC activity as the cytotoxicity.

According to the present invention, the ADCC activity on hematopoietic tumor cells can be measured in the following manner. First, mononuclear cells (E)are isolated as the effector cells from human peripheral blood or bone marrow by the gravity centrifuge method.

As the target cells (T), RPMI8226 (ATCC CCL 155), U266 (ATCC TIB 196), KPMM2, KPC-32, ARH-77 (ATCC CRL 1621), HEL, cells derived from patients or the like is labeled with $^{51}Cr$ to be prepared as the target cells. Subsequently, to the labeled target cells is added the antibody to be measured for the ADCC activity and incubated. Effector cells at a suitable ratio to the target cells are then added and incubated.

After incubation, the supernatant is removed and measured for radioactivity using a gamma counter. At this time 1% NP-40 can be used for measurement of the maximum free radioactivity. The cytotoxicity (%) can be calculated as $(A-C)/(B-C)\times 100$, in which A is radioactivity (cpm) liberated in the presence of the antibody, B is radioactivity (cpm) liberated by NP-40, and C is radioactivity (cpm) liberated by the medium alone containing no antibody.

Enhancement of Cytotoxicity

In order to exhibit cytotoxicity such as an ADCC activity, it is preferred to use Cγ, in particular Cγ1 and Cγ3 as the constant region (C region) of antibody in humans. Furthermore, a more potent ADCC activity or CDC activity can be induced by adding, altering, or modifying part of the amino acids in the C region of antibody.

By way of example, there can be mentioned the conversion of IgG to an IgM-like polymer by amino acid substitution (Smith, R. I. F. & Morrison, S. L. BIO/TECHNOLOGY (1994) 12, 683-688), the conversion of IgG to an IgM-like polymer by amino acid addition (Smith, R. I. F. et al., J. Immunology (1995) 154, 2226-2236), the expression of a tandemly-ligated gene encoding L chain (Shuford, W. et al., Science (1991) 252, 724-727), the dimerization of IgG by amino acid substitution (Caron, P. C. et al., J. Exp. Med. (1992) 176, 1191-1195, Shopes, B., J. Immunology (1992) 148, 2918-2922), the dimerization of IgG by chemical modification (Wolff, E. A. et al., Cancer Res. (1993) 53, 2560-2565), and the introduction of the effector function by altering an amino acid(s) in the hinge region of antibody (Norderhaug, L. et al., Eur. J. Immunol. (1991) 21, 2379-2384) and the like.

These can be accomplished by means of the oligomer site-specific mutagenesis using a primer, the addition of a base sequence using a restriction enzyme cleavage site, and the use of a chemical modifier that creates a covalent bond.

Treatment of Patients

One embodiment of the present invention concerns a method of treating hematopoietic tumors by administering to the patient a pharmaceutical agent that enhances the amount expressed of HM1.24 antigen, and a pharmaceutical agent that induces the expression of HM1.24 antigen in the cell that normally is not expressing HM1.24 antigen on the cell surface and anti-HM1.24 antibody. The hematopoietic tumors are, for example, myeloma, preferably multiple myeloma, lymphocytic tumors such as lymphoma, preferably Hodgkin's disease or non-Hodgkin lymphoma, lymphocytic leukemia, preferably acute T lymphocytic leukemia, chronic T lymphocytic leukemia, acute B lymphocytic leukemia, chronic B lymphocytic leukemia, and myelocytic leukemia for example acute myelocytic leukemia and chronic myelocytic leukemia. Furthermore, acute leukemia belonging to L1-L3 and M0-M7 in the FAB Classification is also included.

A pharmaceutical agent that enhances the amount expressed of HM1.24 antigen, and a pharmaceutical agent that induces the expression of HM1.24 antigen in the cell that normally is not expressing HM1.24 antigen on the cell surface and anti-HM1.24 antibody is preferably interferon-α, interferon-γ, the IRF-2 protein, or a vector containing DNA encoding the IRF-2 protein, and preferably interferon-α and interferon-γ. The dosage of interferon-α and interferon-γ is, when administered to humans, is an amount that attains the highest blood level of 1-10000 I.U./ml (International Units), more preferably 5-1000 I.U./ml, even more preferably 5-500 I.U./ml, and most preferably 5-50 I.U./ml.

In the case of intravenous administration, preferably ten thousand to ten million I.U., more preferably one hundred thousand to ten million I.U., even more preferably fifty thousand to five million I.U., most preferably one million to five million I.U. is given per administration. Interferon and anti-HM1.24 antibody may be administered together or separately. In the latter case, preferably interferon is given first, followed by the administration of anti-HM1.24 antibody within 96 hours. The interval between the interferon administration and the anti-HM1.24 antibody administration is not limited as long as the amount expressed of HM1.24 antigen is being enhanced by the administration of interferon, but it is preferably within 96 hours, more preferably 72 hours, still more preferably 48 hours.

Alternate administration of interferon and anti-HM1.24 antibody for a plurality of times depending on the clinical response of the patient is within the scope of the present invention. The route of administration is preferably given directly into the blood circulation, and intravenous administration or intraarterial administration is preferred. Continued administration is possible and intravenous drip may be used. The administration may also be subcutaneous or intramuscular administration.

Another aspect of the present invention concerns a therapeutic agent or a pharmaceutical composition for the treatment of hematopoietic tumors comprising interferon-α or interferon-γ and anti-HM1.24 antibody. The therapeutic agent of the present invention may contain a pharmaceutically acceptable vehicle that has been used for interferon and antibody preparations, such as physiological saline or 5% dextran, together with a common stabilizer or a excipient.

Another aspect of the present invention provides a kit for treating a patient with hematopoietic tumors, comprising a pharmaceutical composition comprising anti-HM1.24 antibody as an active ingredient and an instruction manual that contains description of combined therapy with interferon-α or interferon-γ.

Another aspect of the present invention provides a pharmaceutical composition comprising anti-HM1.24 antibody as an active ingredient for treating a patient with hematopoietic tumors, wherein said composition is used in combination with interferon-α or interferon-γ.

Another aspect of the present invention relates to the administration of a gene encoding a substance that enhances or induces the expression of HM1.24 antigen. For example, the DNA sequences of interferon-α, interferon-γ, IRF-2 are known and can be administered to patients by integration into the desired vector. As the vector, they are inserted into adenovirus vector (for example pAdexLew) or retrovirus vector (for example pzIPneo), which are then administered to the living body. The method of administration may be ex vivo or in vivo. Alternatively, naked DNA may be administered.

EXAMPLES

Example 1

Enhancement of the Amount of HM1.24 Antigen Expressed in Myeloma Cells by Interferon-α

A human myeloma cell line U266 (ATCC TIB 196) and myeloma cells derived from the bone marrow of a patient with multiple myeloma were cultured in a RPMI1640 medium (Sigma, St Louis, Mo., USA) containing 10% fetal bovine serum (Whittaker Bioproducts, Inc., Walkersville, Md., USA) in a 5% carbon dioxide incubator at 37° C. The hybridoma that produces mouse anti-HM1.24 antibody has been internationally deposited as FERM BP-5233 (deposition date: Apr. 27, 1995) with the National Institute of Bioscience and Human Technology, of 1-3, Higashi 1-chome, Tsukuba city, Ibaraki Pref.

Myeloma cells ($1 \times 10^5$/ml) were cultured in the presence or absence of 1000 U/ml of the natural type interferon-α (otsuka Pharmaceutical, Tokyo) for 48 hours, and changes in HM1.24 antigen (the base sequence encoding this is shown in SEQ ID NO: 1) were determined by flow cytometry. After the cells were washed with phosphate buffer (Gibco BRL, Grand Island, N.Y., USA) supplemented with 0.1% bovine serum albumin (Sigma, St Louis, Mo., USA) and 0.02% sodium azide, they were suspended into PBS (100 μl) supplemented with human immunoglobulin (3 mg/ml, Green Cross, Osaka), and were allowed to react at 4° C. for 15 minutes.

Thereafter, 2 μl of FITC-human IgG1 (1 mg/ml) or FITC-anti-HM1.24 antibody (1 mg/ml) was added to stain at 4° C. for 60 minutes. When the patient's myeloma cells were used, 20 μl of PE-anti-CD38 (Becton Dickinson, San Jose, Calif., USA) was added for double staining to identify the myeloma cells. After staining, the cells were washed twice with PBC, and were stored in PBS containing 1% paraformaldehyde (Wako Pure Chemical Industries, Ltd., Osaka). Subsequently, the expression of HM1.24 antigen was analyzed using a flow cytometer (EPICS XL, Coulter, Hialeah, Fla., USA).

As a result, a myeloma cell line U266 (FIG. 1) and the patient's myeloma cells (FIG. 2) were expressing HM1.24 antigen at a condition of no stimulation, and the stimulation with interferon-α further increased the amount expressed of HM1.24 antigen.

Interferon-α further enhanced the expression of HM1.24 antigen in the myeloma cell, and increased the number of anti-HM1.24 antibodies that bind to the myeloma cell. Since the therapeutic anti-tumor effect by anti-HM1.24 antibody is proportional to the number of antibodies that bound, treatment with anti-HM1.24 antibody after the administration of interferon-α is expected to provide a therapy that enhances the therapeutic effect by antibody and further enhances effectiveness.

Example 2

Analysis of the Expression Function of HM1.24 Antigen by the Reporter Gene Analysis In order to investigate whether the expression induction of antigen is regulated by the HM1.24 promoter region, the reporter gene at the promoter region was analyzed.

The gene (SEQ ID NO: 3) of the HM1.24 promoter region was obtained by PCR cloning. Genomic DNA was prepared from human peripheral blood mononuclear cells using the DNAzol reagent (GIBCO). With the genomic DNA obtained as the template, using primer HM2k (aaaggtaccagctgtctttct-gtctgtcc) (SEQ ID NO: 4) and BST2B (atagtcatacgaagtagat-gccatccag) (SEQ ID NO: 5), PCR (94° C. for 1 min, 55° C. for 1 min, 72° C. for 1 min, 30 cycles) was performed using TaKaRa Taq (Takara Shuzo, Ohtsu) in the Thermal Cycler 480 (Perkin-Elmer, Calif., USA).

An about 2 kb fragment obtained was treated with restriction enzymes KpnI and BglII (Takara Shuzo), and was cloned into the KpnI-BglII site of a reporter gene plasmid pGL3-basic (Promega, Wis., USA) using the DNA ligation kit ver. II (Takara Shuzo) to transform into competent E. coli JM109 (Nippongene). The transformed E. coli was cultured at 37° C. in the LB medium containing 100 μg/ml ampicillin, and the plasmid was prepared using the QIAGEN plasmid maxi kit (QIAGEN, Hilden, Germany).

The plasmid HM-2k/GL3 obtained was treated with restriction enzymes KpnI and XhoI, from which a deletion clone was constructed using the deletion kit (Takara Shuzo) for kilo-sequence to obtain a plasmid HM-493/GL3 containing from the transcription initiation point to −493 bp upstream. Furthermore, HM-2k/GL3 was treated with restriction enzymes KpnI and AflII, from which a deletion clone was constructed as described above, and HM-151/GL3 and HM-77/GL3 containing from the transcription initiation point to −151 bp or −77 bp upstream were obtained.

For the introduction of the plasmid into the cell, the polyethyleneimine-Transferrinfection Kit (Tf PEI-Kit) (Bender MedSystems, Vienna, Austria) was used, and for the luciferase assay the Dual-Luciferase Reporter Assay System (Promega) was used. The cell line was cultured overnight in RPMI-1640 containing 50 μm Defferrioxamine and 10% FBS. In order to form a complex of the plasmid to be introduced with Tf-PEI, a mixture of the reporter gene plasmid at a final concentration of 20 μg/ml, 0.4 μg/ml of pRL-SV40, and 1 μg/ml of Tf-PEI reagent was prepared and was incubated at room temperature for 20 minutes. $5 \times 10^5$ cells/ml of cells were added at three volumes of the Tf-PEI/plasmid mixture, and was incubated at 37° C. for four hours, washed with the medium, and 100 μl per well at a concentration of $2 \times 10^5$ cells/ml was cultured in a 96-well flat-bottomed plate.

IFN-α was added to a final concentration of 0, 10, 100, or 1000 U/ml, which was cultured at 37° C. for two days. After the cells were washed in PBS(−), they were dissolved in 20 μl of the Passive Lysis Buffer, six μl of which was applied to the C96 White Polysorp Fluoronunc plate (Nunc). Using the Luminoskan (Labsystems), luminescence intensity was measured for Firefly and Renila at 30 μl of the substrate solution and a measurement time of 10 seconds. The measured values were corrected by Firefly/Renila, and the relative activity was determined with the control (medium) as one.

As a result, the luciferase activity of the reporter was increased in a IFN-α concentration dependent manner for both of the upstream 2 kbp and 493 bp, confirming that the enhanced transcription activity of the promoter region causes the expression induction of the antigen (FIG. 3).

Figure 4:
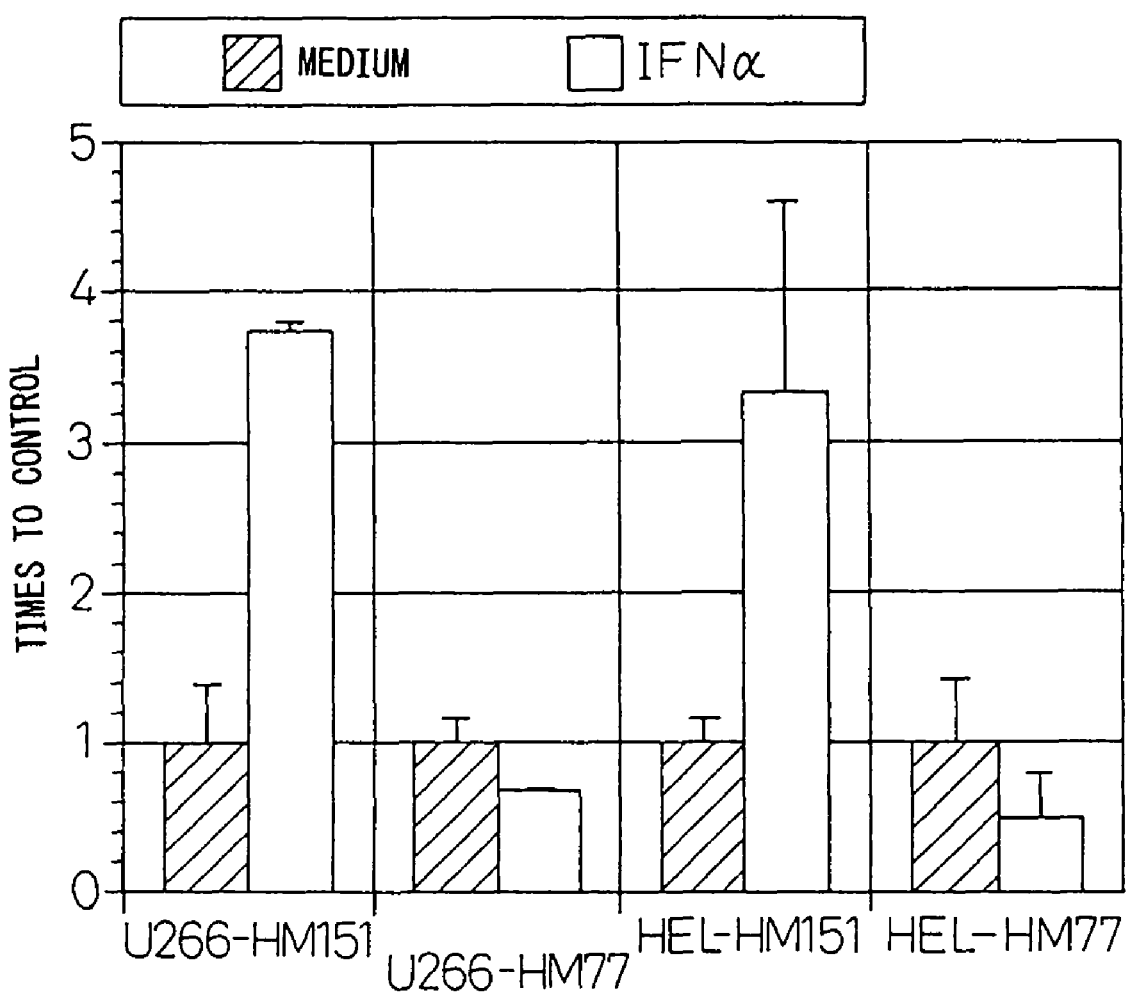
FIG. 4 is a graph showing the result of an experiment in which U266 cells or HEL cells transformed with a reporter plasmid into which a segment from the transcription initiation point to 151 bp upstream or to 77 bp upstream among the promoter region of a gene encoding HM1.24 antigen had been inserted were cultured in the presence of interferon α (1000 U/ml), and then the luciferase activity was determined.

Furthermore, the result of an experiment in which the reporter plasmid 151 bp or 77 bp upstream of the transcription initiation point was used, an enhanced luciferase activity by IFN-α stimulation was observed for the reporter plasmid 151 bp upstream. On the other hand, no changes in activity were noted by IFN-α stimulation in the reporter plasmid 77 bp upstream (FIG. 4). In the region of 77-151 bp, a sequence having a high homology with GAS element and ISRE was present, and since it is a transcription regulatory factor that is activated in response to IFN-α stimulation, the transcription regulatory factor of the IRF family was shown to be involved in the activity.

Example 3

Enhancement of the Amount Expressed of HM1.24 Antigen in Myeloma Cells by Interferon-γ

According to the method described in Example 1, 1000 U/ml of the natural type interferon-γ (R & D System) was used for analysis. As a result, increases in the amount expressed of HM1.24 antigen were observed in both of the myeloma cell line U266 (FIG. 5) and the patient's myeloma cells (FIG. 6) as for interferon-α.

Example 4

Binding of IRF-2 to the HM1.24 Promoter Region

In order to identify the transcription factor that binds to the HM1.24 promoter region, the Electrophoresis Mobility Shift Assay (EMSA) with the HM1.24 promoter region as the probe was performed as follows to identify IRF-2 as the binding factor.
(1) Preparation of Nuclear Extract The myeloma cells U266-B1 (ATCC-TIB196) were cultured in the RPMI-1640 medium (GIBCO-BRL) containing 10% FBS (HyClone) at 37° C. in a 5% $CO_2$ incubator. In order to stimulate the cells by interferon-α (IFN-α) (Pepro Tech EC), IFN-α was added to the medium to a final concentration of 1000 U/ml, and the cells were recovered at 30 minutes, two hours, four hours, and eight hours after the addition. The cells were suspended into cold PBS (−), centrifuged at 1,000 rpm to discard the supernatant, and suspended in a 10 mM Tris, 10 mM NaCl, and 6 mM $MgCl_2$ solution.

After allowing to stand in ice for five minutes, centrifugation was repeated, and the supernatant was discarded. The cells were suspended into 10 mM Tris, 10 mM NaCl, 6 mM $MgCl_2$, 1 mM DTT, 0.4 mM PMSF, 1 mM $Na_3VO_4$. The cells were homogenized on ice using a glass homogenizer, centrifuged at 6000 g for three minutes, and the supernatant was discarded. The cells were suspended into the extraction buffer (20% glycerol, 20 mM HEPES, 420 mM NaCl, 1.5 mM $MgCl_2$, 0.2 mM EDTA, 0.2 mM PMSF, 1 mM DTT, 0.1 mM $Na_3VO_4$, 2 mg/ml aprotinin, and 5 mg/ml leupeptin), and then was allowed to stand in ice for 20 minutes. It was centrifuged at 12000 g for 10 minutes, and the supernatant was recovered.
(2) Preparation of the Labeled Probe As the probe, ISRE2 was constructed that contains sequences (ttcccagaaa (SEQ ID NO: 10) and ggaaactgaaact (SEQ ID NO: 11)) having a homology with GAS (IFN-γ activation site: the GAS consensus sequence is ttncnnnaa (SEQ ID NO: 8)) and ISRE (IFN-α stimulation response factor: the ISRE consensus sequence is ngaaanngaaact (SEQ ID NO: 9)), at the HM1.24 promoter region. Thus, oligo DNA ISRE-F2 (aatttctgggaaactgaaactgaaaacct (SEQ ID NO: 12)) and ISRE-R2 (aattaggttttcagtttcagtttcccaga (SEQ ID NO: 13)) were mixed and annealed to form a double stranded DNA probe ISRE2.

Furthermore, oligo DNA adp-1 (catggcatctacttcgtatgactattgcagagtgcc (SEQ ID NO: 14)) and adp-2 (catgggcactctgcaatagtcatacgaagtagatgc (SEQ ID NO: 15)) were mixed and annealed to form an unrelated probe adp. Probes were labeled using the Band Shift Kit (Amersham Pharmacia Biotech) according to the standard protocol. Thus, 50 ng of double stranded DNA constructed as above was subjected to the polymerase reaction of the Klenow fragment in a reaction solution containing [α-$^{32}$P]dATP (20 μCi) (Amersham Pharmacia Biotech) at 37° C. for one hour. The solution at the end of the reaction was diluted two-fold and then was loaded to the Nick Spin Column (Amersham Pharmacia Biotech), and after centrifugation at 1600 rpm for four minutes, the solution was recovered to prepare a labeled probe.
(3) Changes with Time in the Binding Factor Produced by Stimulation with IFN-α

According to the standard protocol of the Band Shift Kit (Amersham Pharmacia Biotech, N.J., USA), the following procedure was performed. To 5 μg of the extracts prepared as the time elapse in the above (1), were added 2 μl of the 10× biding buffer (100 mM Tris-HCl, pH 7.5, 500 mM NaCl, 5 mM DTT), 4 μl of 50% glycerol, 1 μl of 1% NP-40, and 1 μl of poly(dI-dC)·poly(dI-dC), and then 2 μl of the $^{32}$p labeled ISRE-2 probe prepared in the above (2), to which water was added to a total volume of 20 μl, was added and this reaction mixture was incubated at room temperature for 20 minutes to allow for the binding of the possible binding factors that may be present in the above extract and said $^{32}$P labeled ISRE-2 probe.

To 18 μl of the reaction mixture was added 2 μl of the 10× stain solution (attached to the kit), which was electrophoresed in 1× Tris-glycine buffer (25 mM Tris, 190 mM glycine, 1 mM EDTA, pH 8.1) on a 7.5% acrylamide gel, and then, after electrophoresis, the gel was attached to a filter paper to transfer protein to the filter paper. The filter paper dried with a gel drier was exposed to X-ray film to detect signals.

For comparison, a reaction solution [(NEC−)] to which no extract was added, a reaction solution [0 h] to which an extract from the cell culture that was cultured without stimulation by interferon-α was added, a reaction solution {8 h (+cold)] in which 50 ng of a nonlabeled ISRE2 probe was added in stead of the labeled probe to the extract of 8 hour-culture, and a reaction solution [8 h (+cold unrelated)] in which 50 ng of an unrelated probe adp was added to the extract of 8 hour-culture were prepared, and were processed as described above to detect signals.

Figure 7:
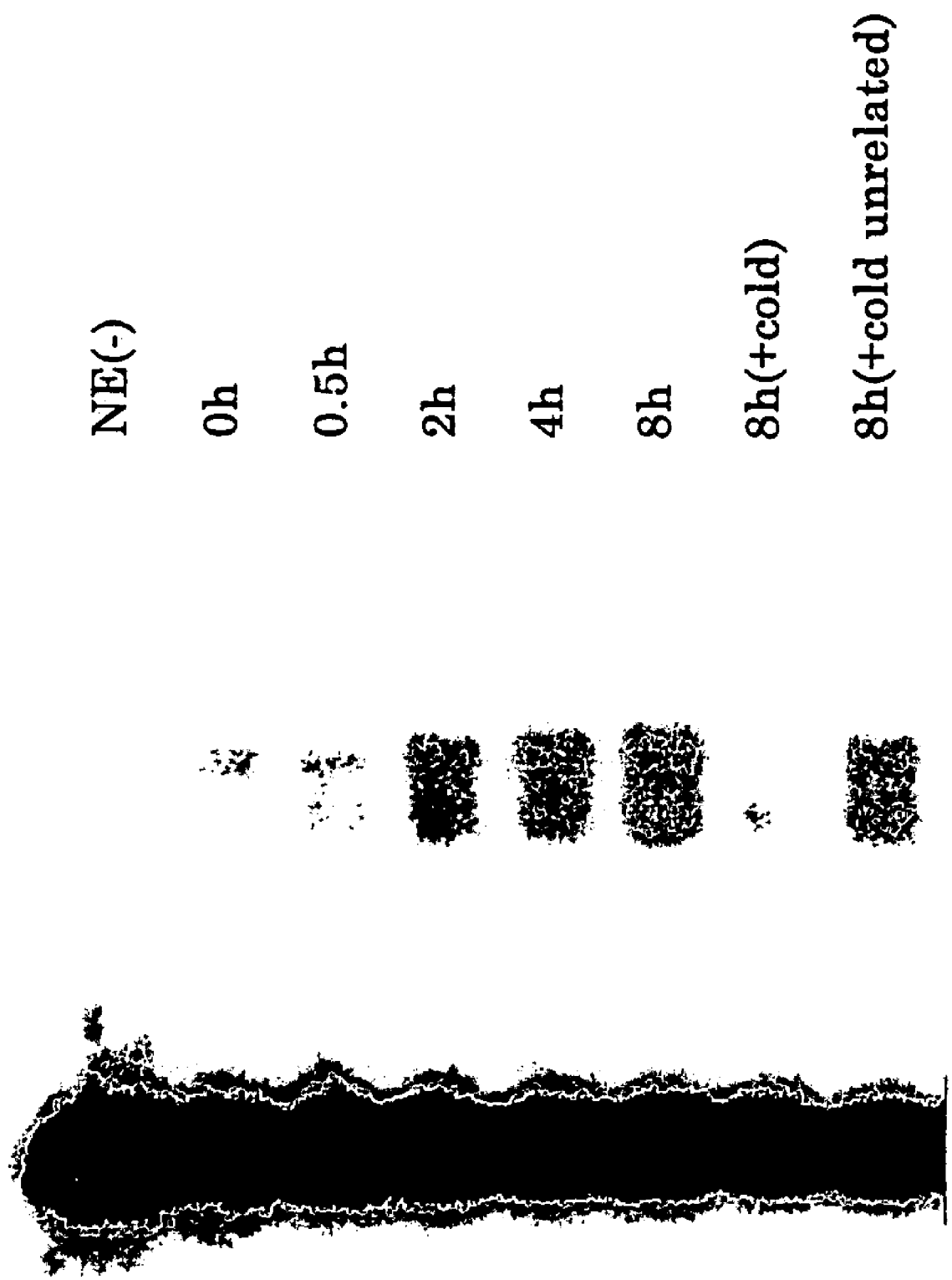
FIG. 7 is an electrophoretogram that shows changes with time in the amount of a transcription factor that is produced by adding IFN a to cultured U266 cells and that binds to the HM1.24 promoter region, and is a photograph substituting for a drawing. NE(−): no nuclear extract was added. Oh: the nuclear extract without IFN-α stimulation was added. 0.5-8 h: the nuclear extracts that passed respective time after stimulation with IFN-α (1000 U/ml) was added. + cold: 50 ng of the nonlabeled ISRE2 probe was added. + cold unrelated: 50 ng of the nonlabeled adp sequence was added.

The result is shown in FIG. 7. As can be seen from this figure, a substance that binds to a double stranded DNA corresponding to part of the HM1.24 promoter increased with time in the U266-B1 cells cultured under the stimulation by interferon.
(4) The Identification of a Transcription Factor by Reaction with Various Antibodies In a manner similar to that described in the above (1), the myeloma cells U266-B1 (ATCC-TIB196) were cultured for eight hours in the presence of 1000 U/ml of interferon-α to prepare an extract. The following procedure was performed according to the standard protocol of the Band Shift Kit (Amersham Pharmacia Biotech). Thus, 2 μg of antibody was added to 5 μg of the extract, and incubated at room temperature for 15 minutes to obtain an extract/antibody reaction solution. To 2 μl of the 10× binding buffer attached to the kit, 4 μl of 50% glycerol, 1 μl of 1% NP-40, and 1 μl of Poly(dI-dC)·Poly(dI-dC) were added 2 μl of the above extract/antibody reaction solution and 2 μl of the labeled probe prepared in the above (2), to which water was added to make the total volume 20 μl, and the reaction mixture was incubated at room temperature for 20 minutes.

The reaction mixture was subjected to electrophoresis as described in the above (3) to detect signals.

As the above antibody, the following antibodies (all are from Santa Cruz Biotechnology) were used:
Anti-human STAT1 p84/p91 (E-23): (description) rabbit polyclonal antibody (SC-346X)

Anti-human STAT2 (C-20): rabbit polyclonal antibody (SC-476X)

Anti-mouse STAT3 (K-15): rabbit polyclonal antibody (SC-483X)

Anti-human ISGF-3γ p48 (C-20): rabbit polyclonal antibody (SC-496X)

Anti-human IRF-1 (C-20): rabbit polyclonal antibody (SC-497X)

Anti-human IRF-2 (C-19): rabbit polyclonal antibody (SC-498X)

Anti-mouse ICSAT (M-17): rabbit polyclonal antibody (SC-6059X)

As a control, a reaction solution that uses an extract of the cells cultured without interferon stimulation [0 h]; a reaction solution in which an extract of the cells cultured for eight hours under the stimulation with 1000 U/ml interferon-α was added, and no antibody was added [8 h]; a reaction solution in which 50 ng of the nonlabeled ISRE2 probe was added instead of the labeled ISRE2 [8 h (+cold)]; and a reaction solution in which 50 ng of the nonlabeled dp probe was added in stead of the labeled ISRE2 probe [8 h (+unrelated cold)] were prepared and processed as described above.

Figure 8:
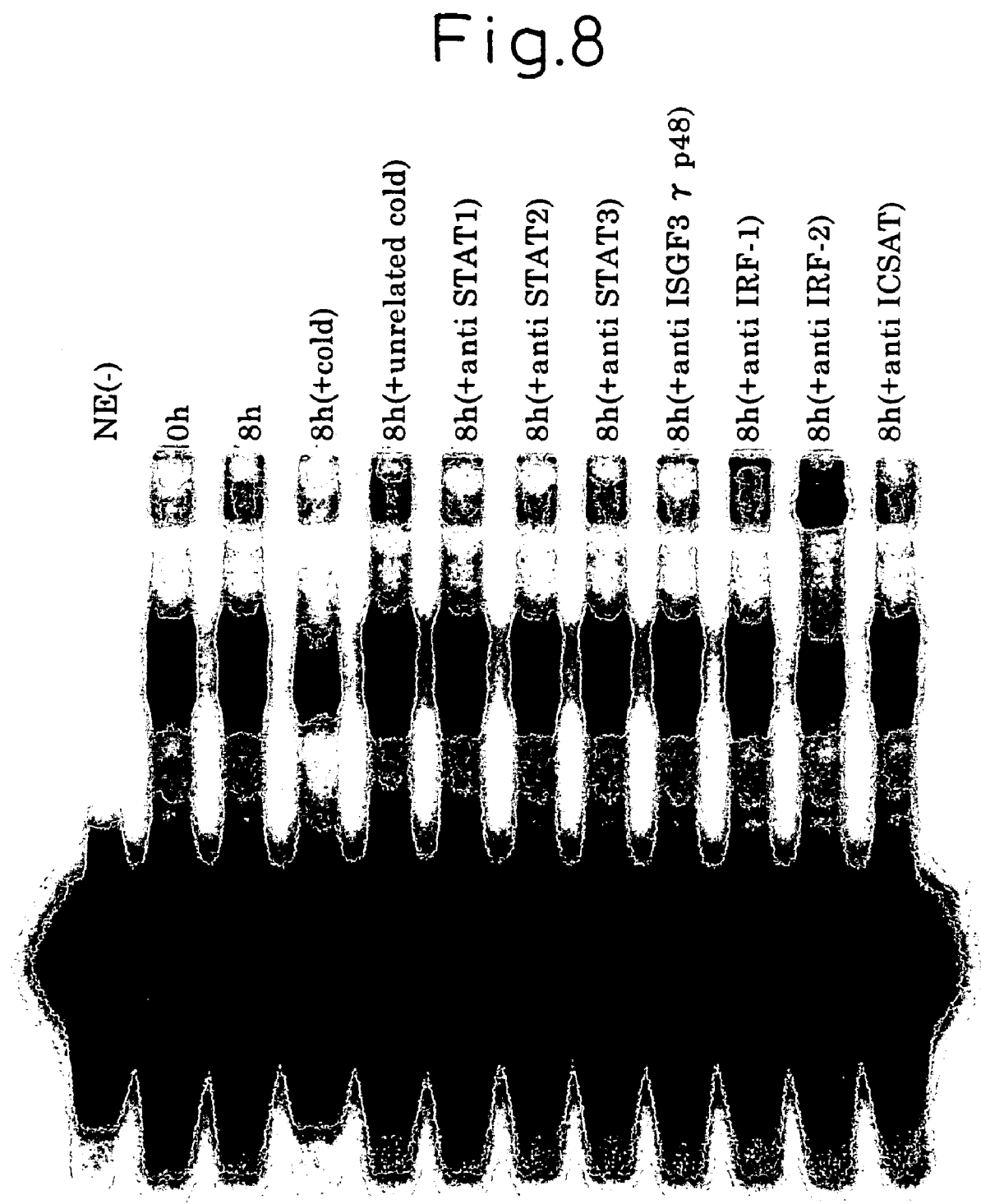
FIG. 8 is an electrophoretogram showing the result of an experiment in which a transcription factor that binds to HM1.24 promoter was identified using various antibodies, and is a photograph substituting for a drawing. NE(−): no nuclear extract was added. Oh: the nuclear extract without IFN-α stimulation was added. 8 h: the nuclear extract 8 hours after stimulation with IFN-α (1000 U/ml) was added. + cold: 50 ng of the nonlabeled ISRE2 probe was added. + cold unrelated: 50 ng of the nonlabeled adp sequence was added. Two μg of each antibody was added.

The result is shown in FIG. 8. As can be seen from this figure, it was shown that the component that binds to the labeled ISRE2 probe in the extract from the cells cultured under the stimulation with interferon-α binds only to anti-IRF-2 antibody, and the factor that binds to and thereby activates the HM1.24 promoter is a transcription factor IRF-2.

Example 5

Confirmation of the HM1.24 Promoter Activation with IRF-2

Effect on HM1.24 promoter activity by IRF-2 co-expression was determined by the reporter gene assay using the U266 cells, and it was revealed that IRF-2 actually has the transcription activation activity of the HM1.24 promoter. In the following experiment, a myeloma cell line U266-B1 (ATCC TIB196) was used. The cells were cultured in the RPMI-1640 medium (GIBCO) (referred to hereinafter as the medium) containing 10% FBS (GIBCO BRL) in an 5% $CO_2$ incubator.

(1) Construction of a Plasmid Containing the HM1.24 Promoter Region

The gene of the HM1.24 promoter region was obtained by PCR cloning. From human peripheral blood mononuclear cells, genomic DNA was prepared using the DNAzol reagent (GIBCO). With the genomic DNA obtained as the template, using primer HM2k (aaaggtaccagctgtctttctgtctgtcc) (SEQ ID NO: 16) and BST2B (atagtcatacgaagtagatgccatccag) (SEQ ID NO: 17), PCR (94° C. for 1 min, 55° C. for 1 min, 72° C. for 1 min, 30 cycles) was performed using TaKaRa Taq (Takara Shuzo, Ohtsu) in the Thermal Cycler 480 (Perkin-Elmer, Calif., USA).

An obtained about 2 kb fragment was treated with restriction enzymes KpnI and BglII (Takara Shuzo), and was cloned into the KpnI-BglII site of a reporter gene plasmid pGL3-basic (Promega, Wis., USA) using the DNA ligation kit ver. II (Takara Shuzo) to transform competent E. coli JM109 (Nippongene). The transformed E. coli was cultured at 37° C. in the LB medium containing 100 μg/ml ampicillin, and a plasmid was prepared using the QIAGEN plasmid maxi kit (QIAGEN, Hilden, Germany).

The plasmid HM-2k/GL3 obtained was treated with restriction enzymes KpnI and XhoI, from which a deletion clone was constructed using the deletion kit (Takara Shuzo) for kilo-sequence to obtain a plasmid HM-491/GL3 containing up to −491 bp upstream of the transcription initiation point. Furthermore, HM-2k/GL3 was treated with restriction enzymes KpnI and AflII, from which a deletion clone was constructed as described above, and HM-151/GL3 containing −151 bp upstream of the transcription initiation point was obtained.

Furthermore, with HM-2k/GL3 as the template, using primer 10S (tttcggtacctaattaatcctctgcctg) (SEQ ID NO: 18) and GL primer 2 (ctttatgtttttggcgtcttcca) (SEQ ID NO: 19), PCR (94° C. for 1 min, 55° C. for 1 min, 72° C. for 1 min, 30 cycles) was performed using TaKaRa Taq (Takara Shuzo, Ohtsu) in the Thermal Cycler 480 (Perkin-Elmer, Calif., USA). The fragment obtained was treated with restriction enzymes KpnI and BglII (Takara Shuzo), and was cloned into the KpnI-BglII site of a reporter gene plasmid pGL3-basic (Promega, Wis., USA) using the ligation high (Toyobo) to transform competent E. coli JM109 (Nippongene).

The transformed E. coli was cultured at 37° C. in the LB medium containing 100 μg/ml ampicillin, and a plasmid was prepared using the QIAGEN plasmid maxi kit (QIAGEN, Hilden, Germany). A plasmid HM-125/GL3 was thus obtained that contains up to 125 bp upstream of the transcription initiation point. Furthermore, with HM-2k/GL3 as the template, using primer HMP700 (aaaggtaccagagtttacctggtatcctgg) (SEQ ID NO: 20) and GL primer 2, PCR was performed in a similar procedure, and by introducing the fragment into the KphI-BglII site of pGL3-basic, HM-700/GL3 containing up to about 700 bp upstream of the transcription initiation point was obtained.

Furthermore, with HM-2k/GL3 as the template, using primer HMP700 and 11A' (cagaggattaattaggtaccgaaagagaggtgggctttt) (SEQ ID NO: 21), PCR (98° C. for 15 seconds, 65° C. for 2 seconds, 74° C. for 30 seconds, 25 cycles) was performed using the KOD polymerase (Toyobo) in the Thermal Cycler 480 (Perkin-Elmer, Calif., USA). The fragment obtained was inserted into the pCR4 Blunt-TOPO vector using the Zero Blunt TOPO PCR cloning kit for sequencing ver. B (Invitrogen). The plasmid obtained was treated with a restriction enzyme KpnI, and an about 550 bp fragment was recovered, which was introduced into the KpnI site of HM-125/GL3 using the ligation high. Thus, dSIRE/GL3 lacking −25 to about −145 upstream of the transcription initiation point was obtained.

(2) Construction of IRF-2 Expression Plasmid

The IRF-2 expression plasmid was constructed as follows. From the U266 cells for which eight hours have elapsed after stimulation with interferon-α (1000 U/ml), total RNA was extracted using the TRIzol reagent (GIBCO BRL). With RNA obtained by using the First-strand cDNA Synthesis kit (Pharmacia) as the template, using NotI-d(T)$_{18}$ as the primer, a reverse transcription reaction was performed at 37° C. for one hour. With the cDNA obtained as the template, using IRF2-F2 (ttgtattggtagcgtgaaaaaagc) (SEQ ID NO: 22) and IRF2-R2 (cagctagttcacattatctcgtcc) (SEQ ID NO: 23) as primers, PCR (94° C. for 45 seconds, 60° C. for 45 seconds, 72° C. for 60 seconds, 40 cycles) was performed using LA-Taq (Takara Shuzo).

With the PCR reaction as the template, using IRF2-F1 (agagggtaccatgccggtggaaaggatgcg) (SEQ ID NO: 24) and IRF2-R1 (agtcggtaccttaactgctcttgacgcggg) (SEQ ID NO: 25) as primers, PCR (94° C. for 45 seconds, 60° C. for 45 seconds, 72° C. for 60 seconds, 30 cycles) was performed using the KOD polymerase (Toyobo). The fragment obtained was treated with a restriction enzyme KpnI, and then introduced into the KpnI site of an expression plasmid pTracer-CMV (Invitrogen) using the ligation high (Toyobo) to obtain a IRF-2 expression plasmid pIRF-2/Tracer.

(3) Measurement of the Reporter Gene Activity

For the introduction of the plasmid into the cells, the polyethyleneimine-Transferrinfection Kit (Tf PEI-Kit) (Bender MedSystems, Vienna, Austria) was used, and for the luciferase assay the Dual-Luciferase Reporter Assay System (Promega) was used. The cell line was cultured overnight in RPMI-1640 containing 50 µM Defferrioxamine and 10% FBS. In order to form a complex of the plasmid to be introduced with Tf-PEI, a mixture of the reporter gene plasmid at a final concentration of 20 µg/ml, 20 µg/ml of pIRF-2/Tracer or pTracer-CMV, 0.4 µg/ml of pRL-SV40, and 1 µg/ml of Tf-PEI reagent was prepared, and was incubated at room temperature for 20 minutes.

$5 \times 10^5$ cells/ml of cells were added at three times the volume of the Tf-PEI/plasmid mixture, and was incubated at 37° C. for four hours, washed with the medium, and 100 µl per well at a concentration of $2 \times 10^5$ cells/ml was cultured in a 96-well flat-bottomed plate. IFN-α was added to a final concentration of 0 or 1000 U/ml, which was cultured at 37° C. for two days. After the cells were washed in PBS(−), the cells were dissolved in 20 µl of the Passive Lysis Buffer, six µl of which was applied to the C96 White Polysorp Fluoronunc plate (Nunc). Using the Luminoskan (Labsystems), luminescence intensity was measured for Firefly and Renila at 30 µl of the substrate at a measurement time of 10 seconds. The measured values were corrected by Firefly/Renila to obtain the correct relative activity.

(4) Result

Figure 9:
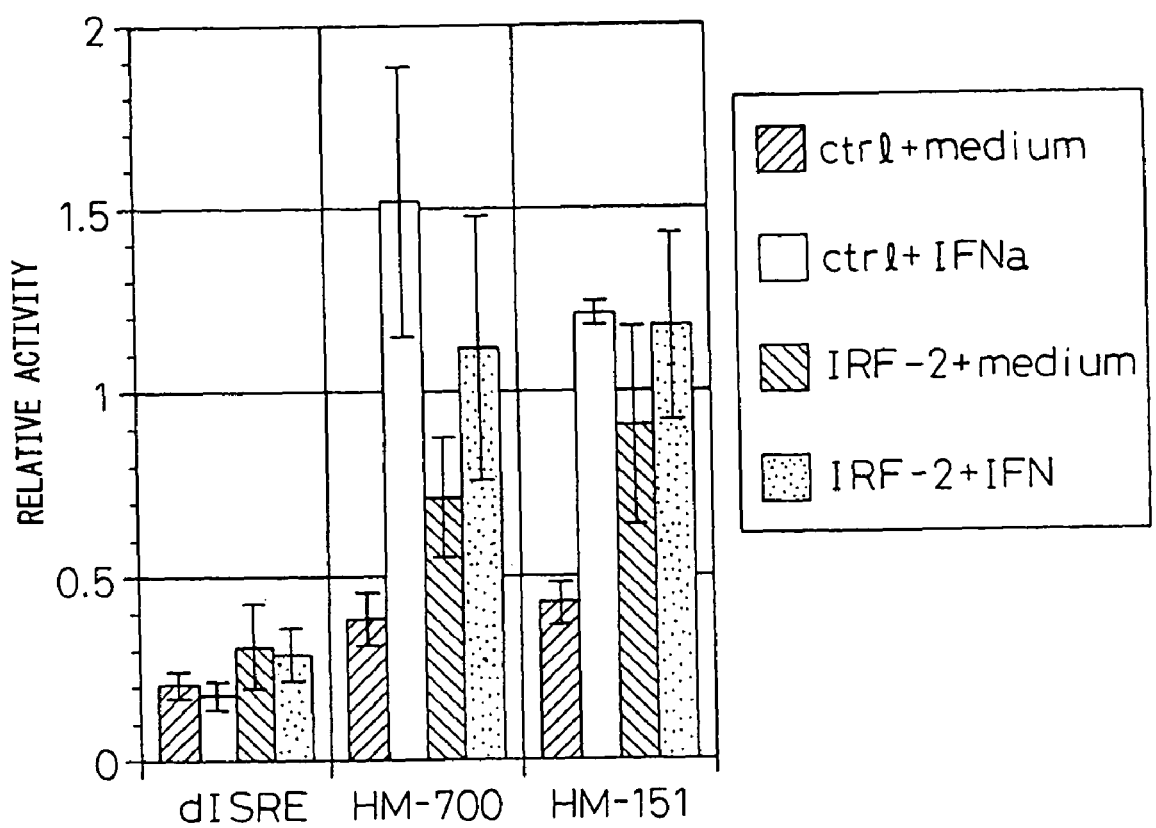
FIG. 9 is a graph showing the result of an experiment in which the HM1.24 promoter reporter plasmid and the IRF-2 expression plasmid were introduced into U266 cells, and the reporter activity was determined.

The HM1.24 promoter reporter plasmid and the IRF-2 expression plasmid were introduced into the U266 cells, and the reporter activity was determined (FIG. 9). As a result, the luciferase activity was increased in −700 and −151 containing the ISRE motif sequence that is a IRF-2 binding site by IRF-2 co-expression. On the other hand, no changes in luciferase activity were noted in dISRE/GL3 that lacks the ISRE sequence by IRF-2 co-expression. This result indicated that IRF-2 binds to the ISRE region of the HM1.24 promoter and enhances its transcription activity.

(5) Confirmation of Enhanced Expression of HM1.24 Antigen by Over Expression of IRF-2

For changes in the amount expressed of HM1.24 antigen by IRF-2, the IRF-2 expression plasmid (PIRF-2/Tracer) or the control plasmid (pTracer/CMV) is introduced into the U266 cells in the method described above, then cultured for 1-2 days, from which the cells are recovered, and then stained with mouse anti-human HM1.24 antibody as a primary antibody. The cells are washed, and further stained with FITC-labeled anti-mouse IgG antibody as a secondary antibody. After washing the cells, the FITC fluorescence intensity of the cells was measured by a flow cytometer. It is confirmed that in the cells in which the IRF-2 expression plasmid was introduced there are more cells having a high FITC intensity compared to the cells in which the control plasmid was introduced.

Example 6

Figure 10:
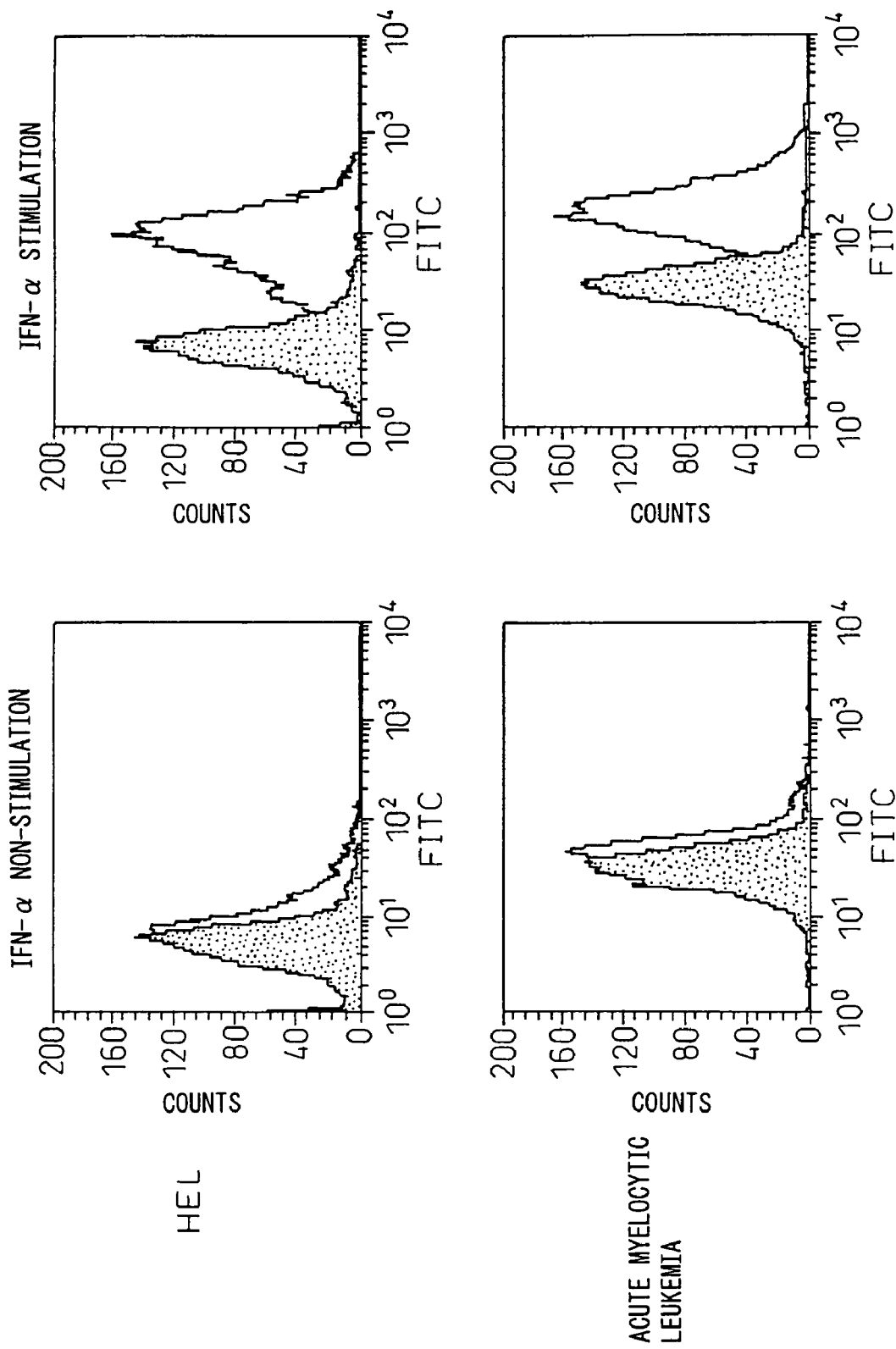
FIG. 10 shows the result of an experiment in which a human leukemia cell line HEL and cells collected from a patient with acute myelocytic leukemia were cultured in the absence (left) or the presence (right) of interferon α, and then were analyzed by flow cytometry using human IgG (control) or anti-HM1.24 antibody as a label. The dark area represents the control and the light area represents the stain with anti-HM1.24 antibody.
Figure 11:
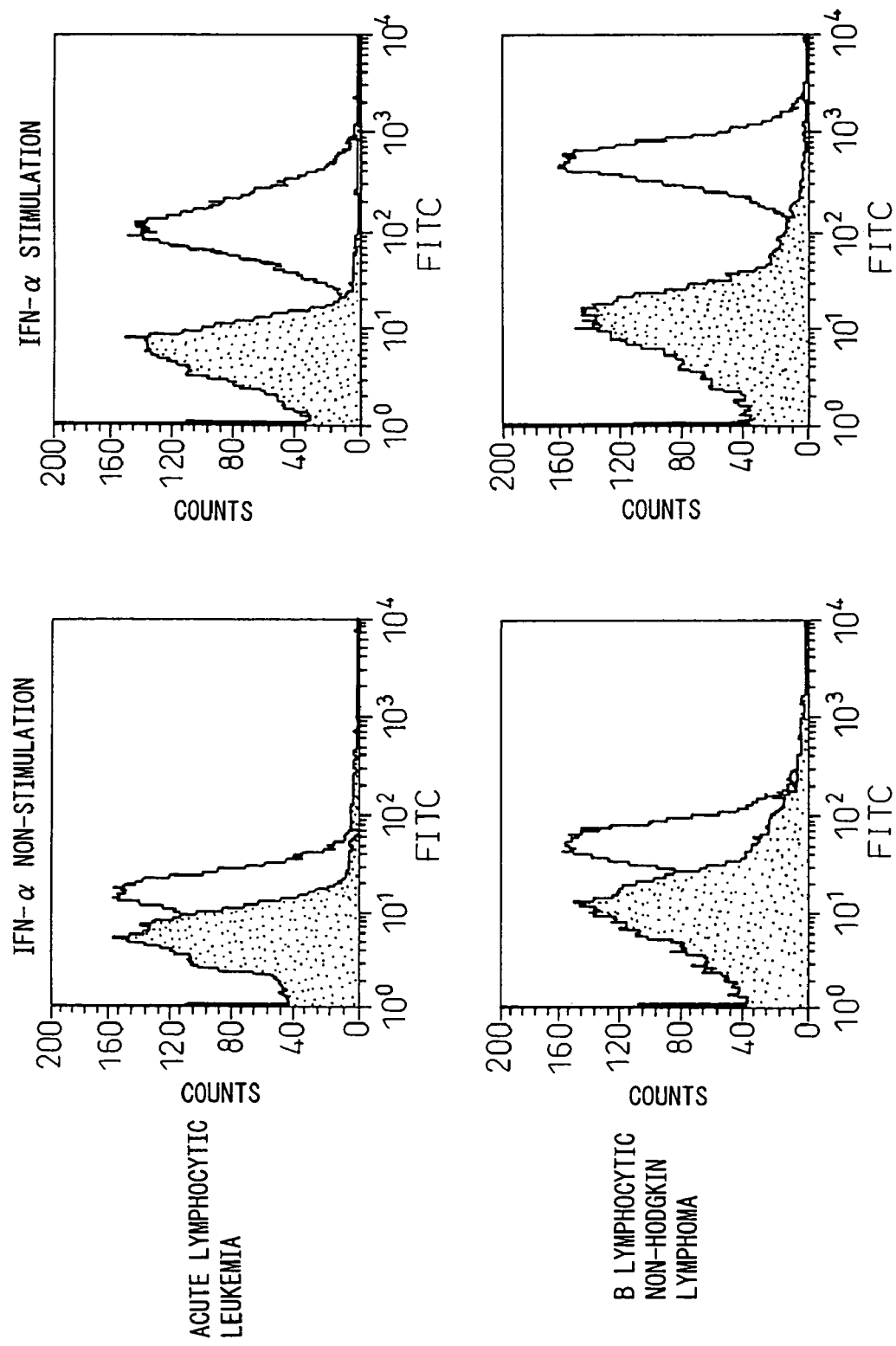
FIG. 11 shows the result of an experiment in which cells collected from a patient with acute lymphocytic leukemia and a patient with B lymphocytic non-Hodgkin lymphoma were cultured in the absence (left) or the presence (right) of interferon α, and then were analyzed by flow cytometry using human IgG (control) or anti-HM1.24 antibody as a label. The dark area represents the control and the light area represents the stain with anti-HM1.24 antibody.

Enhancement of the Amount Expressed of HM1.24 Antigen by Interferon-α in Lymphatic Tumor Cells and Expression Induction of HM1.24 Antigen in Myelocvtic Leukemia Cells A human myelocytic leukemia cell line HEL (Japanese Cancer Research Resources, Tokyo, Japan) and tumor cells derived from the bone marrow and lymph node of patients with hematopoietic tumors were cultured in the method described in Example 1. Interferon-α used is the same as in Example 1, and the method of stimulation by interferon-α and the method of flow cytometry were performed in a similar manner to that described in Example 1. As the FITC-anti-HM1.24 antibody, FITC-humanized anti-HM1.24 antibody (1 mg/ml) was used (see International Patent Publication WO 98/14580, the versions of the light chain and the heavy chain variable region are RVLa and RVHs, respectively). Twenty µl of PE-anti-CD33 antibody for the identification of myelocytic leukemia cells, PE-anti CD19 antibody for the identification of B lymphocytic lymphoma, and PE-anti CD4 antibody (all are from Pharmingen, San Diego, Calif., USA) for the identification of T lymphocytic lymphoma were added, and double-stained (FIGS. 10 to 12).

As a result, under no stimulation with IFN-α, very little or little expression of HM1.24 antigen on the cell surface of HEL and tumor cells derived from patients with acute myelocytic leukemia was observed, indicating that the expression of HM1.24 antigen under no stimulation with IFN-α is substantially not observed in these tumor cells. On the other hand, in tumor cells derived from patients with acute lymphocytic leukemia, B lymphocytic non-Hodgkin lymphoma, and T lymphocytic non-Hodgkin lymphoma, the expression of HM1.24 antigen on the cell surface was observed even under no stimulation with IFN-α. In contrast, when stimulated with IFN-α, the expression of HM1.24 antigen was induced in HEL and tumor cells derived from patients with acute myelocytic leukemia.

In these cells that substantially do not express HM1.24 antigen, IFN-α could cause the expression of HM1.24 antigen. Also, in tumor cells derived from patients with acute lymphocytic leukemia, B lymphocytic non-Hodgkin lymphoma, and T lymphocytic non-Hodgkin lymphoma, the amount expressed of HM1.24 antigen increased. In these five types of tumor cells, the amount of HM1.24 antigen expressed by IFN-α stimulation was almost the same. These results indicate that IFN-α exhibits the effect of inducing or enhancing the expression of HM1.24 antigen for hematopoietic tumor cells in general.

Example 7

Enhancement of ADCC Activity of Anti-HM1.24 Antibody by Interferon α

A human myelocytic leukemia cell line HEL was used as the target cell. To HEL ($1 \times 10^6$ cells), 0.1 mCi of 51 Cr-sodium chromate (New England Nuclear, Boston, Mass., USA) was added and was allowed to stand at 37° C. for 1 hour. Then the cells were washed three times in RPMI1640, and $1 \times 10^4$ cells were dispensed into a round-bottomed 96-well plate (Corning).

After adding various concentrations of humanized anti-HM1.24 antibody (International Patent Publication WO 98/14580, the versions of the light chain and the heavy chain variable region are RVLa and RVHs, respectively), peripheral blood mononuclear cells ($5 \times 10^5$) from normal healthy subjects were added, and were allowed to stand at 37° C. for 4 hours. The radioactivity of the culture supernatant was counted by a gamma counter, and cytotoxicity by ADCC was calculated by the following equation. The maximum value was measured by disrupting the cells by adding 1% NP40 to the target cells. The minimum value was measured by adding the culture liquid RPMI1640 alone (FIG. 13).

ADCC activity (%)=(measured value−minimum value)/(maximum value−minimum value)

As a result, in the absence of stimulation by IFN-α, no concentrations of humanized anti-HM1.24 antibody caused marked ADCC activity. When stimulated by IFN-α, marked ADCC activity due to humanized anti-HM1.24 antibody was noted. Furthermore, ADCC activity was dependent on antibody concentration, which indicated that the expression of HM1.24 antigen on the cell surface induced ADCC activity.

The result indicates that the enhanced amount expressed of HM1.24 antigen on the surface of tumor cells due to stimulation by IFN-α etc. leads to enhancement in cytotoxicity due to anti-HM1.24 antibody, i.e. enhancement in anti-tumor effect and, therefore, that the combined use of an expression-enhancing agent such as IFN-α of anti-HM1.24 antibody could attain an equivalent effect with the use of a smaller amount of anti-HM1.24 antibody. It also indicates that, even in hematopoietic tumor cells for which a marked effect cannot be expected with anti-HM1.24 antibody alone, the combined use of an expression-enhancing agent such as IFN-α and anti-HM1.24 antibody is likely to attain an anti-tumor effect.

The invention claimed is:

1. A method of treating leukemia comprising administering the combination of an expression-enhancing agent for enhancing expression of a protein containing the amino acid sequence set forth in SEQ ID NO: 2 on the cell surface of said tumors and an anti-HM1.24 antibody, wherein the expression-enhancing agent is interferon-α, and wherein said antibody comprises a heavy chain comprising the three heavy chain complementarity determining regions (CDRs) of an antibody produced by a hybridoma having the Deposit No. FERM BP-5233 and a light chain comprises the three light chain CDRs of an antibody produced by said hybridoma.

2. The method according to claim 1, wherein the leukemia is acute myelocytic leukemia, chronic myelocytic leukemia, acute lymphocytic leukemia, or chronic lymphocytic leukemia.

3. The method according to claim 1, wherein the antibody is an antibody having cytotoxicity.

4. The method according to claim 3, wherein said cytotoxicity is ADCC activity.

5. The method according to claim 1, wherein the antibody is a monoclonal antibody.

6. The method according to claim 5, wherein the monoclonal antibody is a chimeric antibody, a humanized antibody, or a human antibody.

7. The method according to claim 1, wherein said antibody is anti-HM1.24 antibody produced by a hybridoma having the Deposit No. FERM BP-5233.

8. The method according to claim 6, wherein the chimeric antibody or humanized antibody is a chimeric antibody or humanized antibody of anti-HM1.24 antibody produced by a hybridoma having the Deposit No. FERM BP-5233.

* * * * *